(12) United States Patent
Spurlock, III

(10) Patent No.: US 11,708,600 B2
(45) Date of Patent: *Jul. 25, 2023

(54) LONG NON-CODING RNA GENE EXPRESSION SIGNATURES IN DISEASE DIAGNOSIS

(71) Applicant: IQUITY, INC., Nashville, TN (US)

(72) Inventor: Charles Floyd Spurlock, III, Nashville, TN (US)

(73) Assignee: DECODE HEALTH, INC., Nashville, TN (US)

( * ) Notice: Subject to any disclaimer, the term of this patent is extended or adjusted under 35 U.S.C. 154(b) by 0 days.

This patent is subject to a terminal disclaimer.

Patent file contains an affidavit/declaration under 37 CFR 1.130(b).

(21) Appl. No.: 16/011,167

(22) Filed: Jun. 18, 2018

(65) Prior Publication Data

US 2019/0106732 A1     Apr. 11, 2019

Related U.S. Application Data

(60) Provisional application No. 62/568,734, filed on Oct. 5, 2017.

(51) Int. Cl.
| | | |
|---|---|---|
| *C12Q 1/6809* | (2018.01) | |
| *C12Q 1/6883* | (2018.01) | |
| *C12Q 1/686* | (2018.01) | |
| *G16H 50/20* | (2018.01) | |
| *G16B 25/00* | (2019.01) | |
| *G16B 40/00* | (2019.01) | |
| *G16B 25/10* | (2019.01) | |
| *G16B 20/00* | (2019.01) | |
| *G16B 40/20* | (2019.01) | |
| *G06F 18/2411* | (2023.01) | |
| *G06F 18/2431* | (2023.01) | |

(52) U.S. Cl.
CPC .......... *C12Q 1/6809* (2013.01); *C12Q 1/686* (2013.01); *C12Q 1/6883* (2013.01); *G06F 18/2411* (2023.01); *G06F 18/2431* (2023.01); *G16B 20/00* (2019.02); *G16B 25/00* (2019.02); *G16B 25/10* (2019.02); *G16B 40/00* (2019.02); *G16B 40/20* (2019.02); *G16H 50/20* (2018.01); *C12Q 2600/112* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 2008/0219985 A1* | 9/2008 | Thompson | A61P 37/00 424/139.1 |
| 2011/0098191 A1* | 4/2011 | Gomez Roman | C07K 14/4703 506/9 |
| 2011/0105731 A1* | 5/2011 | Madison | A61P 43/00 530/387.3 |
| 2011/0177967 A1* | 7/2011 | Carstens | C07K 14/4702 506/9 |
| 2011/0294683 A1* | 12/2011 | Devaux | G01N 33/6893 506/9 |
| 2013/0178428 A1* | 7/2013 | Hoon | C12Q 1/6886 514/19.3 |
| 2013/0267443 A1* | 10/2013 | Chinnaiyan | A61K 31/4184 506/39 |
| 2014/0329242 A1* | 11/2014 | Aune | C12Q 1/6883 435/6.11 |
| 2016/0019337 A1 | 1/2016 | Roberts et al. | |
| 2016/0312283 A1* | 10/2016 | Ounzain | C12Q 1/6883 |
| 2020/0319164 A1* | 10/2020 | Guillonneau | G01N 33/564 |

FOREIGN PATENT DOCUMENTS

| | | |
|---|---|---|
| WO | 2016126844 A1 | 8/2016 |
| WO | 2016196065 A1 | 12/2016 |

OTHER PUBLICATIONS

Aune, TM. et al. Expression of long noncoding RNAs in autoimmunity and linkage to enhancer function and autoimmune disease risk genetic variants. Journal of Autoimmunity, vol. 81, p. 99-109, 2017.*
Zhou, X. et al. Identification of Alzheimer's disease-associated long noncoding RNAs. Neurobiology of Aging, vol. 36, p. 29252931, 2015.*
Chen, D. et al. Plasma long noncoding RNA expression profile identified by microarray in patients with Crohn's disease. World J. Gastroenterology, vol. 22(19), p. 4716-4731, 2016.*
Santoro et al. Expression Profile of Long Non-Coding RNAs in Serum of Patients with Multiple Sclerosis. J. Mol. Neurosci. 59:18-23. (Year: 2016).*
Leveille et al. Enhancer-associated RNAs as therapeutic targets. Expert Opnion on Biological Therapy 15(5):723-734. (Year: 2015).*
Farh et al. Genetic and epigenetic fine mapping of causal autoimmune disease variants. Nature 518:337-344. (Year: 2015).*

(Continued)

*Primary Examiner* — Samuel C Woolwine
(74) *Attorney, Agent, or Firm* — Brown Rudnick LLP; Adam M. Schoen

(57) ABSTRACT

Differential expression of long non-coding RNAs (lncRNAs) and enhancer RNAs (eRNAs) are used to diagnose diseases including neurological diseases, inflammatory diseases, rheumatic diseases, and autoimmune diseases. Machine learning systems are used to identify lncRNAs or eRNAs having differential expression correlated with certain disease states.

6 Claims, 12 Drawing Sheets

Specification includes a Sequence Listing.

(56) References Cited

OTHER PUBLICATIONS

Rong et al. Highly expressed long non-coding RNA FOXD2-AS1 promotes non-small cell lung cancer progression via Wnt/β-catenin signaling. Biochemical and Biophysical Research Communications 484:586-591. (Year: 2017).*

Ensembl web page information for FOXD2-AS1 [online] [retrieved on Apr. 13, 2022] retrieved from http://useast.ensembl.org/Homo_sapiens/Gene/Summary?g=ENSG00000237424;r=1:47432133-47434641;t=ENST00000445551 (Year: 2022).*

Ben-Hur, Asa et al., "Support Vector Clustering", Journal of Machine Learning Research, 2001, vol. 2, pp. 125-137 (13 Pages).

Breiman, Leo, "Random Forests", Machine Learning, 2001, vol. 45, pp. 5-32 (28 Pages).

Chen, Tianqi et al., "XGBoost: A Scalable Tree Boosting System", pp. 1-13 (13 Pages).

Freund, Yoav et al., "A Decision-Theoretic Generalization of On-Line Learning and an Application to Boosting", Journal of Computer and System Sciences, 1997, vol. 55, pp. 119-139 (21 Pages).

Love, Michael I. et al., "Moderated Estimation of Fold Change and Dispersion for RNA-Seq Data with DESeq2", Genome Biology, 2014, vol. 15, pp. 1-21 (21 Pages).

Press, William H. et al., "Numerical Recipes: The Art of Scientific Computing (3rd ed.)", Section 16.5. Support Vector Machines, pp. 883-898, 2007, New York: Cambridge University (27 Pages).

Spurlock, Charles F., "Biogenesis and Transcriptional Regulation of Long Non-Coding RNAs in the Human Immune System" Journal of Immunology, 2016, vol. 197: 4509-4517 (21 Pages).

Tossberg, JT et al., "Gene-Expression Signatures: Biomarkers Toward Diagnosing Multiple Sclerosis", Genes and Immunity, 2012, vol. 13, pp. 146-154 (9 Pages).

International Search Report and Written Opinion dated Jan. 28, 2019, for PCT/US18/54597, filed Oct. 5, 2018.

Luo et al., "Long noncoding RNAs and Alzheimer's disease," Clinical Interventions in Aging, Jun. 29, 2016 (Jun. 29, 2016), vol. 11, pp. 867-872.

Chen et al. "Plasma long noncoding RNA expression profile identified by microarray in patients with Crohn's disease," World Journal of Gastroenterology, May 21, 2016 (May 21, 2016), vol. 22, No. 19, pp. 4716-4731.

Zhang et al. "Long noncoding RNA expression profile in fibroblast-like synoviocytes from patients with rheumatoid arthritis," Arthritis Research & Therapy, Oct. 6, 2016 (Oct. 6, 2016), vol. 18:227, pp. 1-10.

* cited by examiner

| PATIENT | BINARY COMPARISONS | | | | |
|---|---|---|---|---|---|
| | CTRL vs. CIS-MS | CTRL vs. MS-NAIVE | CTRL vs. MS-EST | CTRL vs. OND-I | CIS-MS vs. OND-I |
| CTRL #1 | CTRL | CTRL | CTRL | CTRL | CIS-MS |
| CIS-MS #1 | CIS-MS | MS-NAIVE | MS-EST | OND-I | CIS-MS |

FIG. 9

|  |  | mRNA | | | | lncRNA | | | |
|  |  | RATIOSCORE | | VALIDATION | | RATIOSCORE | | VALIDATION | |
| CASE | CONTROL | Ratios | Accuracy | Accuracy | ROC | Ratios | Accuracy | Accuracy | ROC |
|---|---|---|---|---|---|---|---|---|---|
| CTRL | CTRL-UFM | 50 | 65.7 | 87.7 | 0.89 | 38 | 95.2 | 97.1 | 0.97 |
| CTRL | CIS-MS | 38 | 77.6 | 82.7 | 0.69 | 15 | 92.7 | 88.6 | 0.79 |
| CTRL | MS-NAÏVE | 38 | 90.0 | 91.7 | 0.89 | 21 | 88.3 | 89.8 | 0.87 |
| CTRL | MS-EST | 73 | 76.4 | 79.2 | 0.79 | 52 | 92.5 | 77.6 | 0.77 |
| CTRL | OND-I | 47 | 89.6 | 86.0 | 0.88 | 28 | 97.8 | 89.3 | 0.87 |
| CTRL | OND-NI | 40 | 86.2 | 89.0 | 0.88 | 36 | 93.0 | 86.4 | 0.87 |
| CTRL-UFM | CIS-MS | 25 | 98.7 | 92.1 | 0.91 | 14 | 87.8 | 93.5 | 0.89 |
| CTRL-UFM | MS-NAÏVE | 23 | 94.4 | 98.5 | 0.99 | 21 | 83.3 | 92.2 | 0.91 |
| CTRL-UFM | MS-EST | 37 | 98.4 | 99.1 | 0.99 | 36 | 96.2 | 91.3 | 0.92 |
| CTRL-UFM | OND-I | 27 | 97.6 | 97.3 | 0.95 | 21 | 95.5 | 91.4 | 0.91 |
| CTRL-UFM | OND-NI | 22 | 99.1 | 97.3 | 0.97 | 25 | 96.0 | 91.8 | 0.91 |
| CIS-MS | MS-NAÏVE | 32 | 87.8 | 75.6 | 0.75 | 21 | 100.0 | 82.0 | 0.82 |
| CIS-MS | MS-EST | 42 | 98.0 | 86.6 | 0.73 | 41 | 99.2 | 86.5 | 0.80 |
| CIS-MS | OND-I | 29 | 80.3 | 76.0 | 0.75 | 13 | 100.0 | 90.6 | 0.88 |
| CIS-MS | OND-NI | 24 | 96.1 | 91.7 | 0.90 | 14 | 100.0 | 94.3 | 0.93 |
| MS-NAÏVE | MS-EST | 48 | 98.8 | 89.4 | 0.89 | 27 | 99.2 | 91.1 | 0.92 |
| MS-NAÏVE | OND-I | 35 | 88.9 | 90.2 | 0.90 | 20 | 100.0 | 83.8 | 0.85 |
| MS-NAÏVE | OND-NI | 20 | 97.8 | 96.1 | 0.96 | 23 | 99.0 | 92.5 | 0.91 |
| MS-EST | OND-I | 54 | 84.3 | 77.7 | 0.76 | 23 | 96.6 | 94.6 | 0.93 |
| MS-EST | OND-NI | 58 | 94.1 | 83.7 | 0.84 | 30 | 82.0 | 91.4 | 0.92 |
| OND-I | OND-NI | 45 | 96.0 | 88.3 | 0.89 | 26 | 95.0 | 93.6 | 0.93 |

FIG. 10A

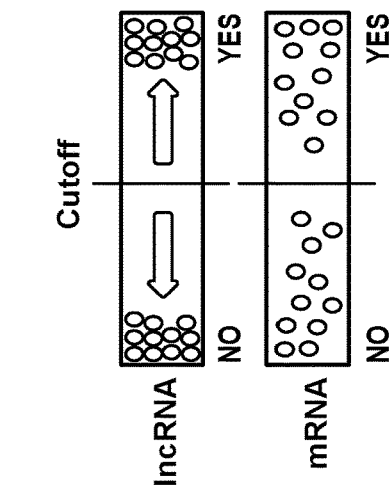
FIG. 11A
FIG. 11B
FIG. 11C
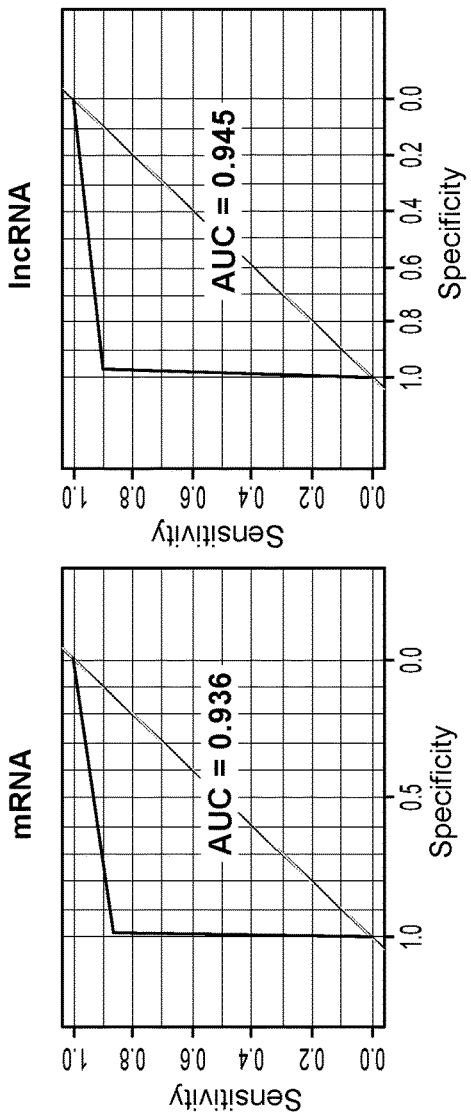
Optimized Multi-category Classification Results
| Class | mRNA | | | lncRNA | | |
|---|---|---|---|---|---|---|
| | Accuracy | Sensitivity | Specificity | Accuracy | Sensitivity | Specificity |
| Multiple sclerosis | .94 | .97 | .90 | .95 | .98 | .92 |
| Other neurologic diseases *inflammatory* | .95 | .92 | .99 | .98 | .98 | .97 |
| Other neurologic diseases *non-inflammatory* | .95 | .91 | .99 | .98 | .98 | .99 |
FIG. 11D

LONG NON-CODING RNA GENE EXPRESSION SIGNATURES IN DISEASE DIAGNOSIS

RELATED APPLICATION

The present application claims the benefit of and priority to U.S. provisional patent application Ser. No. 62/568,734, filed Oct. 5, 2017, the contents of which are incorporated by reference herein in their entirety.

TECHNICAL FIELD

The disclosure relates to detecting disease using differential expression of long non-coding or enhancer RNA.

BACKGROUND

While the understanding of disease has expanded greatly in recent decades, there are still many serious diseases that the medical community is ill-equipped to diagnose and treat. Many of those diseases exhibit improved outcomes if detected and treated early. Due to a reliance on subjective analysis and diagnoses of exclusion (diagnosing by process of elimination) many patients receive late diagnoses of diseases such as multiple sclerosis (MS) and can suffer shortened life expectancies and a lower quality of life as a result. Because diseases like MS are degenerative and loss of function is cumulative, early detection and treatment can afford significant benefits in delaying further degenerative changes and attacks while patients who begin treatment later do not reap the same benefits as those who begin treatment earlier during the disease course.

Furthermore, many diagnostics have high false positive rates, which can lead to unnecessary and potentially harmful treatment in addition to the confusion and unwarranted trauma of misdiagnosis. Standard diagnostic techniques for diseases, such as MS and others, are done by lengthy testing and elimination of other conditions. There are many other diseases (e.g., rheumatoid arthritis (RA), systemic lupus erythematosus (SLE), and fibromyalgia syndrome (FMS)) that rely on diagnoses of exclusion or are otherwise difficult to diagnose resulting in increased patient suffering, wasted resources, and worse clinical outcomes due to delayed or ineffective treatment. Methods for rapid and accurate diagnosis are still lacking for many conditions.

SUMMARY

The present invention provides methods for disease diagnosis and identification through the analysis of differentially expressed long non-coding RNA (lncRNA) or enhancer RNA (eRNA) species. Long non-coding RNA are regulatory RNA molecules that are not believed to code for proteins but that influence a vast array of biological processes. They are generally longer than about 200 nucleotides. The eRNA are a class of non-coding RNA between about 50 and about 2000 nucleotides in length that are transcribed from enhancer regions of DNA. The present invention recognizes that certain lncRNAs and eRNAs are differentially expressed in various diseases and can therefore be used as signatures for those diseases through relatively inexpensive, quick, and simple assays on, for example, patient blood (including serum and plasma) samples. By measuring expression levels of these non-coding RNAs in patients, early diagnosis is made for difficult-to-diagnose diseases, such as MS, with high sensitivity, and specificity. Accordingly, methods and kits of the present invention provide a reliable diagnostic tool that is non-invasive and inexpensive enough to allow for widespread disease screening. Early treatment and better outcomes for patients are therefore benefits afforded by the present invention.

Methods of the invention are used to diagnose large classes of disease, such as neurological diseases, inflammatory diseases, rheumatic diseases, gastrointestinal diseases, cardiovascular disease, psychiatric disease (e.g., PTSD) and autoimmune diseases, among others. Specific diseases that are diagnosed using methods of the invention include, for example, multiple sclerosis (MS), Parkinson's disease, Alzheimer's disease, epilepsy, Crohn's disease, ulcerative colitis, IBD (inflammatory bowel disease), systemic lupus erythematosus, rheumatoid arthritis, and fibromyalgia. In certain embodiments, methods of the invention are used to diagnose various types of cancer.

Methods of the invention are used to diagnose patients in response to the development of certain symptoms or, given the low cost and high potential reward of early diagnosis, could be used to test or screen seemingly healthy patients. Methods of the invention may be used to determine disease progression or grade. In certain embodiments, methods of the invention relate to identifying lncRNAs or patterns of lncRNAs that exhibit differential expression at various disease states through, for example, machine learning analysis of lncRNA or eRNA expression data in patient cohorts with known disease outcomes.

Aspects of the invention may include methods for screening for, identifying or diagnosing the presence of disease. For example, methods of the invention include isolating ribonucleic acid (RNA) from a patient sample, conducting an assay on the RNA to measure an expression level of a long non-coding RNA (lncRNA), and determining presence of a disease where the expression level is different than a reference expression level. The reference level can be taken from healthy populations or from populations having a disease that is not the target of the screen or diagnostic. For example, a reference lncRNA signature for the determination of IBS may be taken from a population of patients identified as having colorectal cancer. Alternatively, the reference population may be healthy individuals.

Methods of the invention may include measuring expression levels of a plurality of lncRNA species and determining presence of disease where the expression levels are different than expected reference expression levels. In certain embodiments, methods of the invention may include distinguishing between FMS, RA, and SLE based on differential expression levels of lncRNA species.

The invention is useful, for example, to diagnose disease may be Parkinson's disease, Alzheimer's disease, epilepsy, Crohn's disease, ulcerative colitis, IBD (inflammatory bowel disease), systemic lupus erythematosus, rheumatoid arthritis, or fibromyalgia. Patient samples include, for example, blood, saliva, sputum, urine, semen, transvaginal fluid, cerebrospinal fluid, sweat, stool, a cell or a tissue biopsy. In certain embodiments, the assay includes a reverse transcription polymerase chain reaction (RT-PCR). Quantitative RT-PCR can be used to provide quantitative analysis of species expression.

Methods of the invention may include conducting an assay on the RNA to measure an expression level of a housekeeping gene and normalizing the expression level of the lncRNA species to the expression level of the housekeeping gene. The housekeeping gene can be GAPDH, ACTB, B2M, 18S, or 28S. Methods of the invention may also include prescribing or administering a treatment regimen to the patient based on the determination of the presence of a disease. For example, methods may include prescription of or administration of ocrelizumab, beta interferons, glatiramer acetate, dimethyl fumarate, fingolimod, teriflunomide, natalizumab, alemtuzumab, or mitoxantrone upon determination of the presence of MS based on lncRNA species expression. In certain embodiments, methods may include providing a written report of the lncRNA species expression levels along with a disease determination and/or recommended treatments based on those expression levels.

In certain aspects, the invention includes methods of identifying biomarkers indicative of a disease. For example, expression levels of lncRNA from samples obtained from patients known to have a particular disease are curated and introduced to a machine learning algorithm as a training set. Unknown samples are then applied to the algorithm for diagnosis. The training algorithm may be a standard machine learning algorithm or may be a custom design. In any case, the algorithm learns to associate differential expression of lncRNA and/or eRNA or a combination thereof) with disease status, disease types, progression, or other measures of disease state. When an unknown sample is presented, the algorithm determines the likelihood that the patient is affected. That may be done by a simple matching algorithm or other means as determined by the programmer.

The machine learning algorithm can include one or more of a random forest, a support vector machine (SVM), and a boosting algorithm.

Methods may include calculating ratios between each pair of expression levels of the plurality of lncRNA species and providing the ratios to the machine learning system.

Aspects of the invention can include a kit comprising primer pairs for determining expression levels of one or more lncRNA species found to be differentially expressed in individuals having a disease. In certain embodiments, the disease may be MS. In certain embodiments, the diseases may be FMS, RA, and SLE and the primers may be selected from SEQ ID NOs: 1-92

In certain aspects, the invention is used to screen for the presence of disease. Ribonucleic acid (RNA) is isolated from a patient sample and an assay is conducted on the RNA to measure an expression level of a enhancer RNA (eRNA) or lncRNA species, and determining presence of a disease where the expression level is different than a reference expression level wherein the disease is selected from the group consisting of a neurological disease, an inflammatory disease, a rheumatic disease, and an autoimmune disease.

BRIEF DESCRIPTION OF THE DRAWINGS

FIG. 9 shows an exemplary vector of binary classifier output used to train hybrid-classifier or multi-category classifier.

FIG. 10A compares accuracy various machine learning systems trained as binary classifiers using differentially expressed mRNAs and lncRNAs.

FIG. 11A depicts ROC curves of mRNA.

FIG. 11B depicts ROC curves of lncRNA.

FIG. 11C diagrams trends in confidence of MS machine learning predictions of lncRNA and mRNA species.

FIG. 11D compares optimized multi-category or hybrid classifiers for mRNAs and lncRNAs.

DETAILED DESCRIPTION

Figure 1:
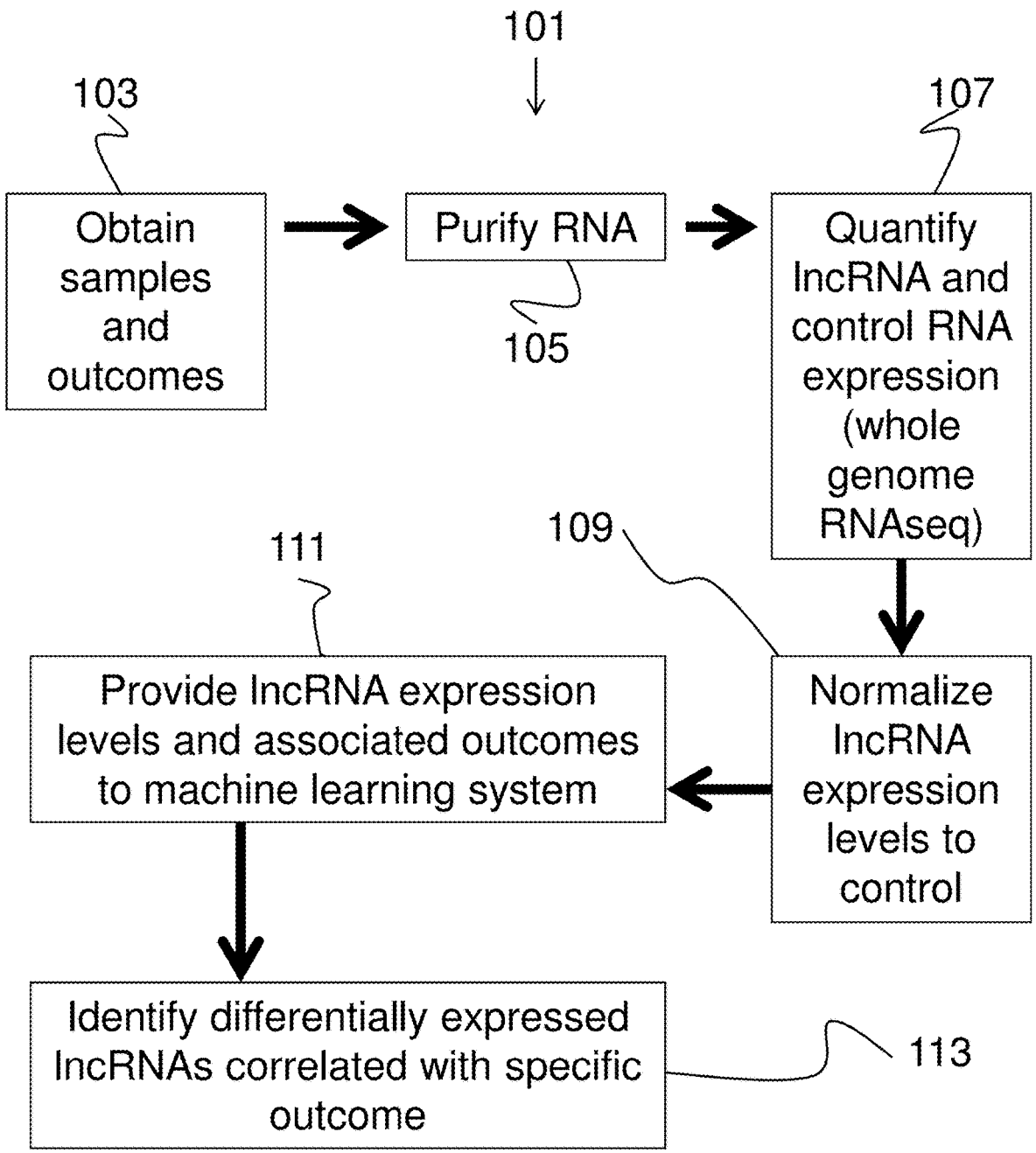
FIG. 1 diagrams steps of a machine learning method for identifying lncRNAs differentially expressed in specific disease states.

Methods and kits of the invention relate to identifying the presence of disease based on differential expression of one or more lncRNAs or eRNAs in a patient sample. Measuring differential expression of various lncRNAs or eRNAs can provide a cheap and accurate diagnostic tool for various hard to diagnose neurological diseases, inflammatory diseases, rheumatic diseases, and autoimmune diseases. By providing accurate and early diagnoses of degenerative diseases such as MS, kits and methods of the invention allow for earlier and better treatment of the disease, prolonging life expectancies, increasing patients' quality of life, and avoiding unnecessary or harmful treatment. In various embodiments, methods of the invention provide for diagnosis of diseases such as multiple sclerosis (MS), Parkinson's disease, Alzheimer's disease, epilepsy, Crohn's disease, ulcerative colitis, IBD (inflammatory bowel disease), systemic lupus erythmatosus, rheumatoid arthritis, and fibromyalgia through analysis of expression levels of one or more lncRNAs or eRNAs and comparison to threshold expression levels. Increased or decreased expression of certain RNAs or patterns of increased and/or decreased expression of a plurality of RNAs can indicate the presence of particular diseases with accuracy, specificity, and sensitivity all above 90%. The expression levels may be determined through assays such as RT-PCR performed on RNA obtained from patient samples such as blood. By providing for accurate disease diagnosis from a simple blood draw, methods and kits of the invention constitute a significant advance over existing diagnostic techniques for diseases such as MS. Because of the reduced costs and the non-invasive nature of the claimed techniques, methods of the invention may be applied to apparently healthy individuals in screens at yearly physicals to allow for even earlier detection and treatment of diseases including degenerative disorders like MS or Alzheimer's. Screens may be implemented based on risk factors such as family medical history. In certain embodiments, the invention provides kits comprising primer pairs for determining expression levels of lncRNAs or eRNAs associated with various diseases as discussed herein.

In various embodiments, methods of the invention relate to identifying lncRNAs or eRNAs that are differentially expressed in particular diseases or classes or disease through machine-learning analysis of expression levels and disease outcomes from groups of patients.

Long non-coding RNAs (lncRNAs) are regulatory RNA molecules that do not code for proteins but influence a vast array of biological processes. See Spurlock, et al., 2016, Biospeciesis and transcriptional regulation of long non-coding RNAs in the human immune system, Journal of Immunology, 197:4509-4517, incorporated herein by reference. The lncRNA designation is generally restricted to non-coding transcripts longer than about 200 nucleotides. The length designation differentiates lncRNA from small regulatory RNAs such as short interfering RNA (siRNA) and micro RNA (miRNA). In vertebrates, the number of lncRNA species is thought to greatly exceed the number of protein-coding species. It is also thought that lncRNAs drive biologic complexity observed in vertebrates compared to invertebrates. Evidence of this complexity is seen in many cellular compartments of a vertebrate organism such as the T lymphocyte compartment of the adaptive immune system. Without wishing to be tied to a particular theory, it is believed that differences in expression and function of lncRNAs are major contributors to complex human disease. Methods of the invention recognize that lncRNA expression may be associated with certain diseases and exhibit far greater differences in expression than disease-associated mRNAs. Accordingly, lncRNAs, which may have been overlooked by researchers because they do not code for proteins, can in fact provide keen insights into disease through comparative measurements of their expression in patients.

eRNAs are non-coding RNA molecules between 50-2000 nucleotides that are transcribed from enhancer regions of DNA. eRNA expression has been found to correspond to the activity of its enhancer. eRNAs have been implicated in transcriptional regulation. eRNA and lncRNA classifications can overlap in instances of eRNA longer than about 200 nucleotides. Like lncRNAs, eRNA has not traditionally been treated as a biomarker for disease, probably due to its non-coding status however, the present invention recognizes that certain eRNAs, a with lncRNAs, can exhibit distinct expression signatures based on certain disease states. Methods and kits of the invention rely on these signatures to diagnose and treat otherwise difficult to detect diseases. Methods and kits described herein may be equally applied to identify differentially expressed, disease associated lncRNAs and eRNAs. Descriptions herein that refer only to either lncRNA or eRNA alone should be understood to be equally applicable to either.

In certain embodiments, methods of the invention may be used to determine unique lncRNA or eRNA signatures associated with specific diseases. Expression levels for known and unknown lncRNA or eRNA sequences may be determined using, for example, RNA-Seq or whole transcriptome shotgun sequencing for a series of samples from patients with known disease outcomes. For example, known whole genome sequencing techniques such as TruSeq whole-transcriptome analysis from Illumina, Inc., (San Diego, Calif.) may be used. RNA can be selected based on size during library preparation (e.g., targeting RNA longer than 200 nucleotides) using techniques such as size exclusion gel or size selection magnetic beads. Analysis tools such as TopHat2 (Johns Hopkins University for Computational Biology), Cufflinks (University of Washington, Cole Trapnell Lab), and DESeq2 (See Love M I, Huber W and Anders S, 2014, Moderated estimation of fold change and dispersion for RNA-seq data with DESeq2, Genome Biology, 15, pp. 550, incorporated herein by reference) may be used to align RNA sequences and to determine expression levels and identify differential expression of lncRNA or eRNA. RNA may be obtained from patient biological samples such as blood, saliva, sputum, urine, semen, transvaginal fluid, cerebrospinal fluid, sweat, breast milk, nipple aspirate, stool, a cell or a tissue biopsy.

In preferred embodiments, samples may be peripheral whole blood. Blood can be collected from subjects having known disease status or from test subjects and may be analyzed immediately or stored in, for example, PAXgene Blood RNA tubes available from Qiagen N.V. (Hilden, Germany) or other RNA stabilizing storage mechanisms. RNA may be isolated and purified or cleaned using commercially available kits such as the PAXgene RNA kit available from Qiagen N.V. (Hilden, Germany).

By comparing expression levels of lncRNAs and eRNAs in healthy and diseased patients one can identify lncRNAs or eRNAs that are differentially expressed in patients having certain diseases or disease outcomes. In certain embodiments, the lncRNA and/or eRNA expression data and associated known outcomes may be subjected to machine learning analysis to identify patterns of differential expression most predictive of disease. lncRNA or eRNA levels may by normalized against measured expression levels of a housekeeping gene from the same sample. Suitable housekeeping gene may include GAPDH, ACTB, B2M, 18S, and 28S.

FIG. 1 shows steps of an exemplary method 101 for identifying lncRNAs associated with specific diseases using machine learning systems. In the exemplary method of FIG. 1, samples from patients with known disease states are obtained 103 as described above and RNA may be extracted and purified 105 using the techniques mentioned earlier. Differentially expressed lncRNAs are identified from whole genome sequencing data 107. The data may be normalized to expression levels of controls (e.g., housekeeping species) 109. Differentially expressed lncRNAs are provided to a machine learning system, along with the known disease states of the patients from whom the differentially expressed lncRNAs were obtained 111. The machine learning system is used to identify lncRNAs with over or under expression most correlated with specific disease states 113.

Methods of the invention may include applying a ratio-score analysis to the expression levels. See, Tossberg J T, Crooke P S, Henderson M A, Sriram S, Mrelashvili D, Chitnis S, Polman C, Vosslamber S, Verweij C L, Olsen N J, Aune T M: Gene-expression signatures: biomarkers toward diagnosing multiple sclerosis. Gene Immun 2012, 13:146-154, incorporated herein by reference. Through the application of ratioscore analysis, expression ratios of two species rather than a single species can be used as inputs for subsequent machine learning systems. By using species ratios, the data can be normalized independent of any measured housekeeping gene and does not rely on the housekeeping gene being consistently expressed at the same level across samples.

Additionally, by using ratios of over-expressed species to under-expressed species, a greater quantitative difference can be produced than when using a single species. For example, if one species is consistently over-expressed by two-fold and a second species is consistently under-expressed by two-fold, then the ratio of the two species would produce a fourfold difference in a case-control comparison. All possible ratios can be calculated and then optimized through, for example, permutation testing to identify the most strongly correlated ratios to the disease. By the above method, the smallest number of ratios representing the maximum separation between healthy and disease groups can be determined.

Expression levels or, in preferred embodiments, the ratio values determined using ratioscore analysis above, can be input along with their associated patient outcomes into various machine learning algorithms to identify differentially expressed lncRNAs or eRNAs or patterns or combinations thereof that are most indicative of the outcome being tested for.

While the above methods have been primarily described for identifying patients having a particular disease, the same techniques can be applied to expression profiles linked to patient outcomes such as disease prognosis, positive response to particular treatments, or differentiating between two diseases that produce similar symptoms. By analyzing expression levels from populations with any of the above differing outcomes, patterns of differential expression having diagnostic value can be determined.

Any machine learning algorithm may be used to analyze RNA differential expression levels including, for example, a random forest, a support vector machine (SVM), or a boosting algorithm (e.g., adaptive boosting (AdaBoost), gradient boost method (GSM), or extreme gradient boost methods (XGBoost)), or neural networks such as H2O. Machine learning algorithms generally are of one of the following types: (1) bagging, (2) boosting, or (3) stacking.

In bagging, multiple prediction models (generally of the same type) are constructed from subsets of classification data (classes and features) and then combined into a single classifier. Random Forest classifiers are of this type. In boosting, an initial prediction model is iteratively improved by examining prediction errors. Adaboost.M1 and eXtreme Gradient Boosting are of this type. In stacking models, multiple prediction models (generally of different types) are combined to form the final classifier. These methods are called ensemble methods. The fundamental or starting methods in the ensemble methods are often decision trees. Decision trees are non-parametric supervised learning methods that use simple decision rules to infer the classification from the features in the data. They have some advantages in that they are simple to understand and can be visualized as a tree starting at the root (usually a single node) and repeatedly branch to the leaves (multiple nodes) that are associated with the classification.

Random forests use decision tree learning, where a model is built that predicts the value of a target variable based on several input variables. Decision trees can generally be divided into two types. In classification trees, target variables take a finite set of values, or classes, whereas in regression trees, the target variable can take continuous values, such as real numbers. Examples of decision tree learning include classification trees, regression trees, boosted trees, bootstrap aggregated trees, random forests, and rotation forests. In decision trees, decisions are made sequentially at a series of nodes, which correspond to input variables. Random forests include multiple decision trees to improve the accuracy of predictions. See Breiman, L. Random Forests, Machine Learning 45:5-32 (2001), incorporated herein by reference. In random forests, bootstrap aggregating or bagging is used to average predictions by multiple trees that are given different sets of training data. In addition, a random subset of features is selected at each split in the learning process, which reduces spurious correlations that can results from the presence of individual features that are strong predictors for the response variable.

SVMs can be used for classification and regression. When used for classification of new data into one of two categories, such as having a disease or not having a disease, a SVM creates a hyperplane in multidimensional space that separates data points into one category or the other. Although the original problem may be expressed in terms that require only finite dimensional space, linear separation of data between categories may not be possible in finite dimensional space. Consequently, multidimensional space is selected to allow construction of hyperplanes that afford clean separation of data points. See Press, W. H. et al., Section 16.5. Support Vector Machines. Numerical Recipes: The Art of Scientific Computing (3rd ed.). New York: Cambridge University (2007), incorporated herein by reference. SVMs can also be used in support vector clustering. See Ben-Hur, A., et al., (2001), Support Vector Clustering, Journal of Machine Learning Research, 2:125-137.

Boosting algorithms are machine learning ensemble meta-algorithms for reducing bias and variance. Boosting is focused on turning weak learners into strong learners where a weak learner is defined to be a classifier which is only slightly correlated with the true classification while a strong learner is a classifier that is well-correlated with the true classification. Boosting algorithms consist of iteratively learning weak classifiers with respect to a distribution and adding them to a final strong classifier. The added classifiers are typically weighted in based on their accuracy. Boosting algorithms include AdaBoost, gradient boosting, and XGBoost. Freund, Yoav; Schapire, Robert E (1997). "A decision-theoretic generalization of on-line learning and an application to boosting". Journal of Computer and System Sciences. 55: 119; S. A. Solla and T. K. Leen and K. Müller. Advances in Neural Information Processing Systems 12. MIT Press. pp. 512-518; Tianqi Chen and Carlos Guestrin. XGBoost: A Scalable Tree Boosting System. In 22nd SIGKDD Conference on Knowledge Discovery and Data Mining, 2016; the contents of each of which are incorporated herein by reference.

Figure 8:
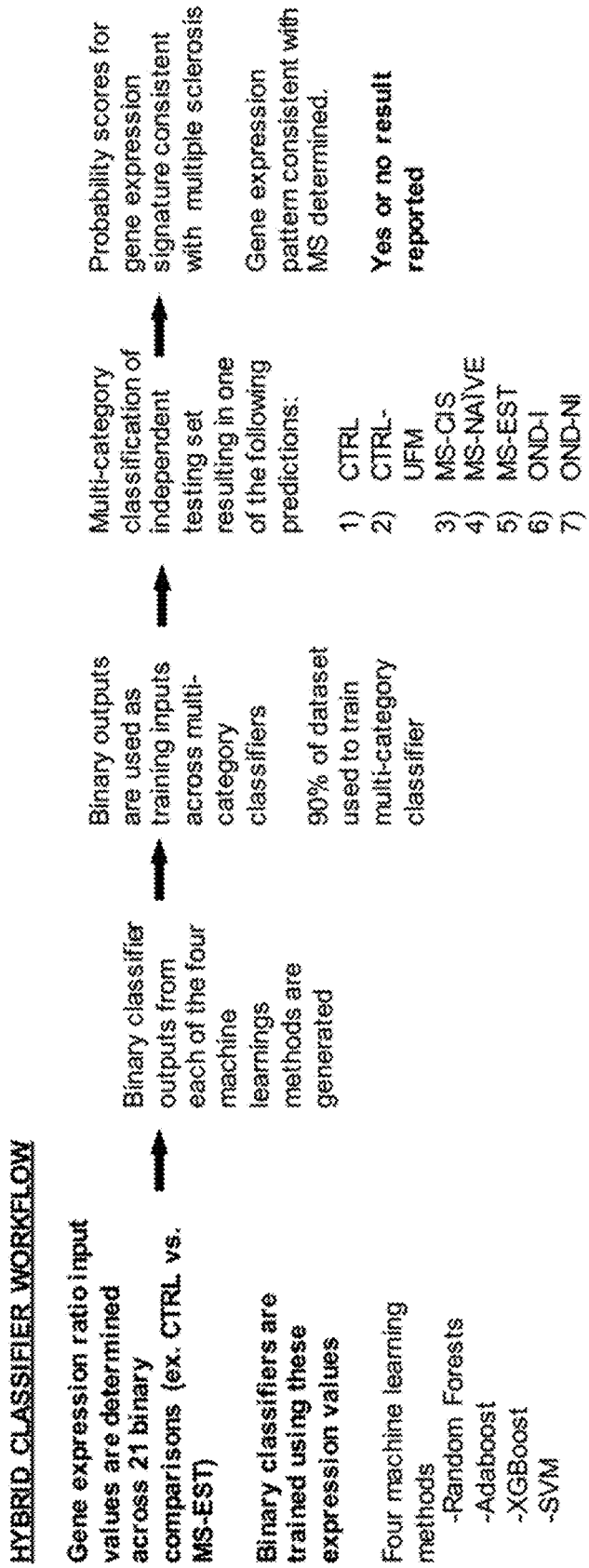
FIG. 8 diagrams a hybrid classification workflow.

In certain embodiments, a hybrid classifier system may be used to distinguish between patients with different disease states as discussed herein. For example, a series of independent classifiers can be used to generate outputs that are evaluated in a second set of inputs to create a multi-category classification based only the comparisons. Accordingly, such methods can be used to overcome some of the shortcomings of machine learning techniques applied to multi-category classification while taking advantage of those machine learning techniques strong binary classifications. FIG. 8 diagrams a hybrid classification workflow. Binary classifiers are trained using measured lncRNA or eRNA expression data from paired categories of patient populations (e.g., any two of: positive for disease A, positive for disease B, or healthy). Outputs from those binary classifiers are generated using a plurality of machine learning methods (e.g., random forests, AdaBoost, XGBoost, and SVM) and then used as inputs in a multi-category analysis (e.g., classifying among 3 or more categories such as positive for disease A, B, C, or D) using one or more machine learning methods as described above. In certain embodiments, hybrid classifiers may be created as follows: Trained binary classifiers capable of discriminating individual subclasses (e.g. disease states) can be applied to a dataset comprising lncRNA expression levels. For each control and disease class, the output of the binary classifiers can be used to create a vector for each patient in the dataset. An exemplary vector is shown in FIG. 9. The vectors may then be used to train each multi-category classifier. Different combinations of input binary classifiers and multi-category classifiers can be used. Training and application of hybrid classifiers using mRNA expression levels are described in U.S.

Methods of the invention include diagnostic tests based on measured lncRNA or eRNA expression levels. After lncRNAs or eRNAs have been identified as being differentially expressed in certain disease states, their expression levels may be measured in test subjects with unknown disease status and used to diagnose those patients.

Figure 2:
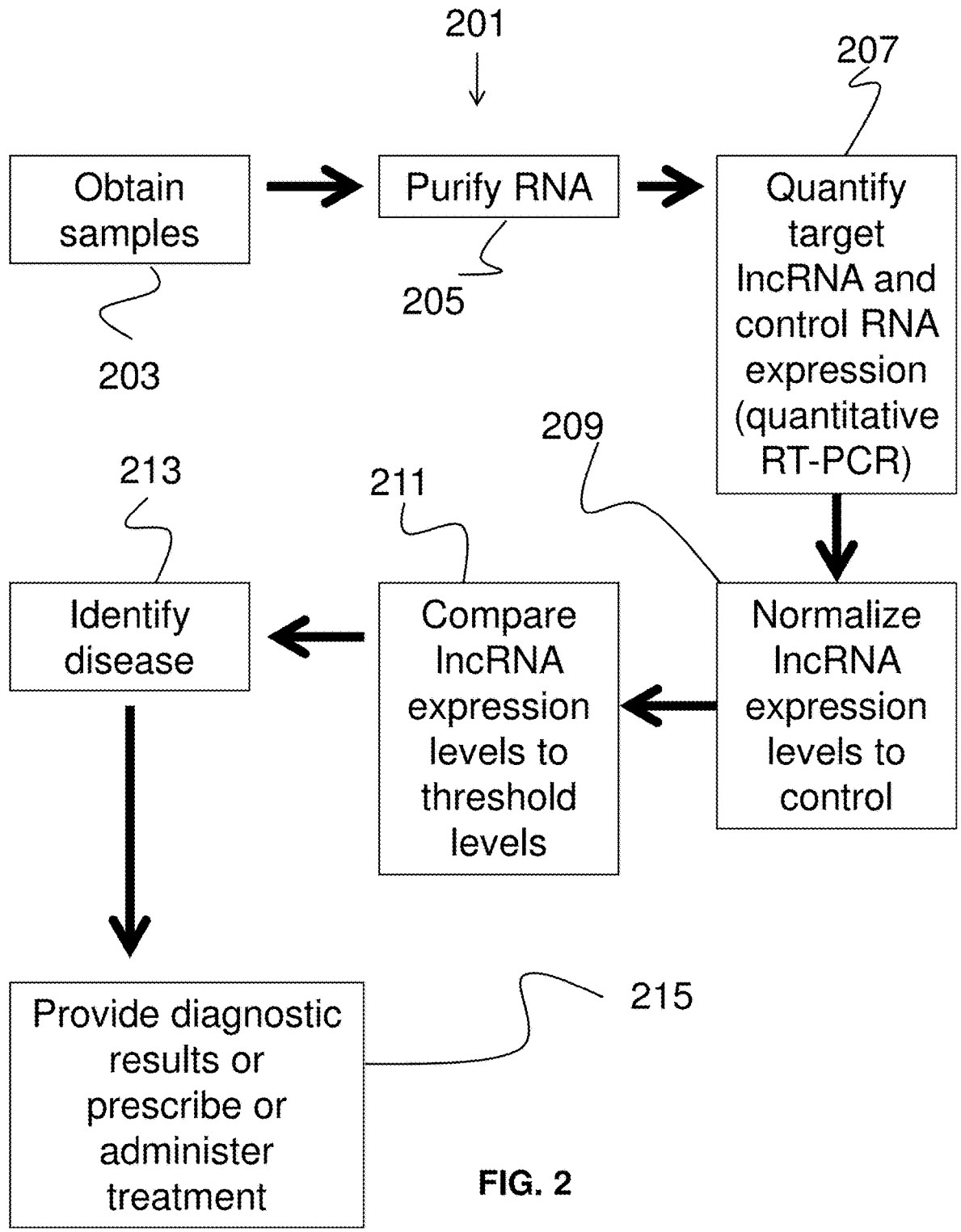
FIG. 2 diagrams steps of an exemplary method for diagnosing disease based on differential expression of lncRNAs.

FIG. 2 shows an exemplary method 201 for diagnosing a patient. In the exemplary method, a sample is obtained from a patient 203. The sample may comprise blood, saliva, sputum, urine, semen, transvaginal fluid, cerebrospinal fluid, sweat, breast milk, nipple aspirate, stool, a cell or a tissue biopsy. RNA can be isolated from the sample using any known technique and may be stored and/or purified 205 as described above. Expression of target lncRNAs and control RNAs (e.g., housekeeping species) are then quantified 207. Quantification may be accomplished through quantitative RT-PCR using primers designed to amplify lncRNAs that are over or under expressed in certain disease states. Expression data may be normalized 209 to expression levels of a housekeeping gene or other control measured in the sample. In certain embodiments, pairs of lncRNAs or eRNAs may be analyzed to determine expression ratios that may be indicative of disease as described above. The normalized expression levels may be compared 211 to a threshold level for each respective lncRNA and, based on over or under expression of one or more lncRNAs compared to their respective thresholds, a disease may be identified 213 that corresponds to that pattern of differential expression. Threshold expression levels may be determined, for example, by measuring average expression of the lncRNA or eRNA in a cell line (e.g., Jurkat cells or other human cell lines). In certain embodiments, thresholds may be determined from expression levels in healthy relatives of the patient or may be compared to expression levels in earlier samples from the patient. The patient may thereby be diagnosed with the disease and may be provided with the diagnosis, or prescribed or administered treatment for the diagnosed disease 215.

For example, where the disease is MS, methods may include prescription or administration of ocrelizumab, beta interferons, glatiramer acetate, dimethyl fumarate, fingolimod, teriflunomide, natalizumab, alemtuzumab, or mitoxantrone. Where the disease is RA, methods may include prescription or administration of physical therapy, anti-inflammatories, steroids, or immunosuppressive drugs. Where the disease is FMS, methods may include prescription or administration of pain medication, nerve blocking, muscle relaxants, or a selective serotonin reuptake inhibitor (SSRI). Where the disease is SLE, methods may include prescription or administration of steroids or immunosuppressive therapies.

Kits and methods of the invention may be directed at screening for the presence of a disease in a subject. Diseases contemplated by the invention include, for example neurological diseases, inflammatory diseases, rheumatic diseases, and autoimmune diseases. In certain embodiments, diseases may be any non-cancer disease. Diseases may be inflammatory neurological diseases (e.g., acute disseminated encephalomyelitis, Bell's palsy, CNS lupus, Guillaine Bane, myasthenia gravis, neuromyelitis optica, optic neuritis, and transverse myelitis) or non-inflammatory neurological diseases (e.g., Alzheimer's, cerebral ataxia, cerebral bleed, cervical radiculopathy, drug-induced movement disorder, dystonia, epilepsy, essential tremor, Huntington's disease, hydrocephalus, median neuropathy, meningioma, migraine, Parkinson's disease, pseudotumor, restless leg syndrome, seizures, spasmodic torticollis, stroke, Tourette's syndrome, and transient ischemia). In certain embodiments, screened-for diseases may include all non-cancer diseases.

In certain embodiments, methods may include measuring expression levels of one or more lncRNA species and determining presence of disease where the expression levels are different than reference expression levels. The disease may be multiple sclerosis (MS) and the lncRNA species can include any species associated with a signature for MS.

Kits for diagnosing FMS may include primers designed to amplify one or more of the above lncRNA species. Exemplary primers may comprise the sequences listed below in Table 1. In certain embodiments, primers may share about 90% sequence identity with the primers listed in Table 1.

Kits for diagnosing rheumatoid arthritis may include primers designed to amplify one or more of the above lncRNA species. Exemplary primers may comprise the sequences listed below in Table 4. In certain embodiments, primers may share about 90% sequence identity with the primers listed in Table 2.

Kits for diagnosing Systemic Lupus Erythromatosis may include primers designed to amplify one or more of the above lncRNA species. Exemplary primers may comprise the sequences listed below in Table 3. In certain embodiments, primers may share about 90% sequence identity with the primers listed in Table 3.

In certain embodiments, methods of the invention may include distinguishing between FMS, RA, and SLE based on differential expression levels of lncRNA species.

In various embodiments, the disease may be Parkinson's disease, Alzheimer's disease, epilepsy, Crohn's disease, ulcerative colitis, IBD (inflammatory bowel disease), systemic lupus erythmatosus, rheumatoid arthritis, or fibromyalgia.

In certain embodiments, kits of the invention include a plurality of primers designed to amplify lncRNAs that are differentially expressed in specific disease states. Kits may be directed at a specific disease such as MS, FMS, RA, or SLE or other inflammatory or non-inflammatory neurological diseases or may include a panel capable of identifying differentially expressed lncRNAs associated with a plurality of individual disease. The latter kits may serve as a multi-disease screening tool and may be useful in differentiating between multiple difficult to diagnose diseases with similar symptoms (e.g., FMS, RA, and SLE).

EXAMPLES

Example 1

Peripheral whole blood was collected into PAXgene tubes from healthy control subjects (N=8), and MS patients at three different stages in the diagnostic process (1) patients with a clinically isolated syndrome (8) who later developed multiple sclerosis (CIS→MS; n=6), (2) MS patients at the time of diagnosis prior to the initiation of therapies (MS-naïve; n=6), and (15) MS patients greater than or equal to 1 year after diagnosis receiving different therapies (MS-established; n=6). Total RNA from PAXgene tubes was used to prepare sequencing libraries using the Illumina Tru-Seq RNA kit with oligo-dT as the primer. 100 bp paired-end reads were generated with an Illumina Hi-Seq 2500. A quality control step was initially performed using tools such as Fastx Toolkit and FastQC (30-34). The RNA data were aligned with TopHat2 and species expression levels were quantified using Cufflinks and are reported as FPKM (fragments per kilobase per million reads). Differentially expressed species were determined using DESeq2. False discovery rate (FDR<0.05) was used for multiple test correction. GTF files for messenger RNAs and long non-coding RNAs were obtained from GENCODE (release 19; GRCh37.p13). A 0.5 FPKM cutoff was used for lncRNAs and mRNAs across these sequencing data.

Figure 3:
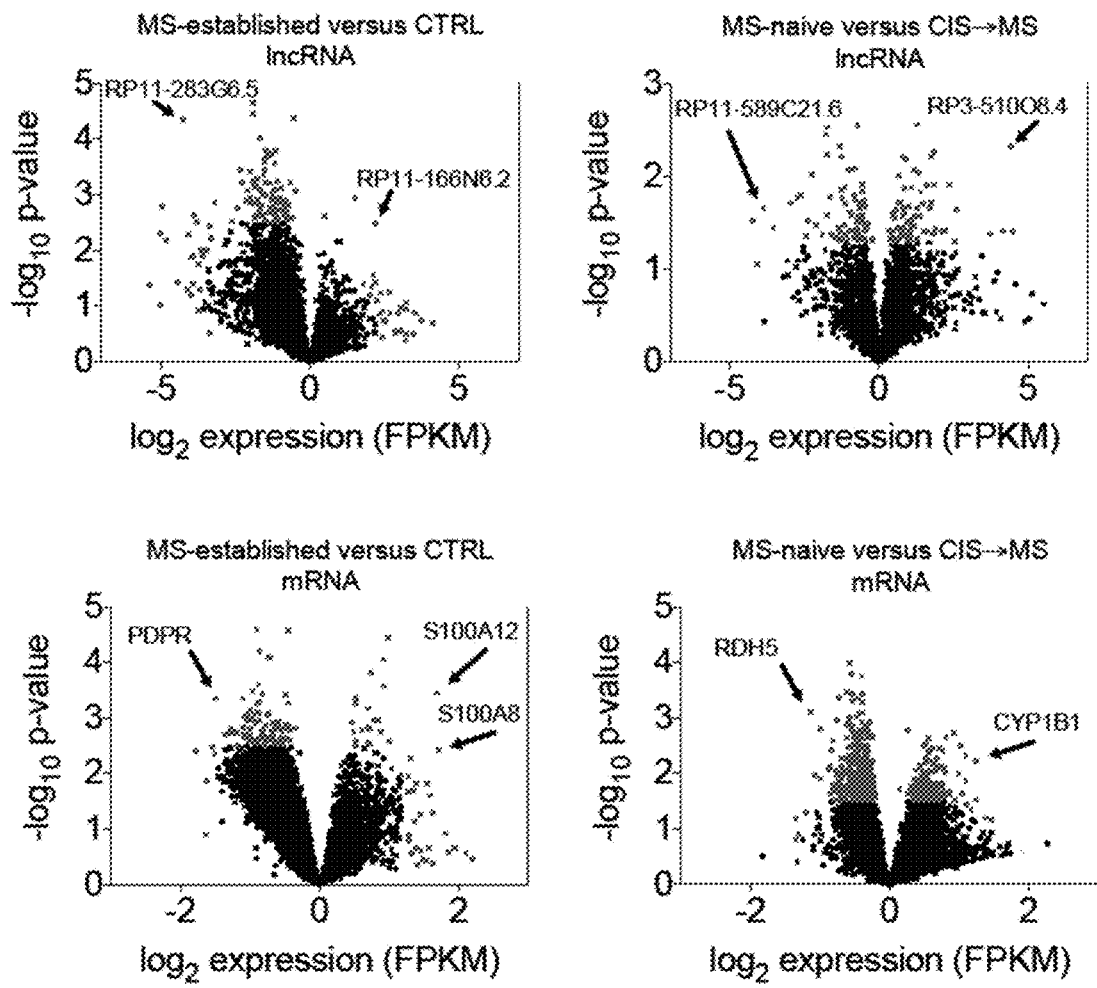
FIG. 3 shows differential expression of unique lncRNAs and mRNAs between MS, control, and distinct stages of MS.
Figure 4:
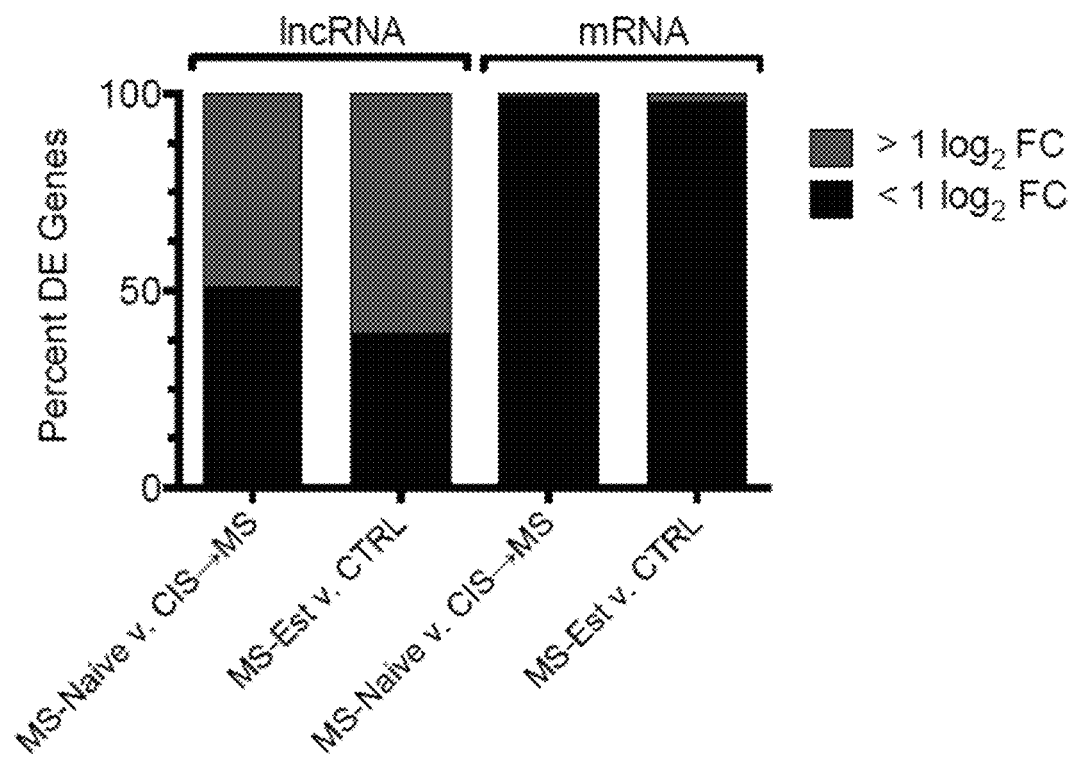
FIG. 4 shows magnitude of fold-change differences across mRNA and lncRNA species at distinct stages of multiple sclerosis.

Volcano plots are shown in FIG. 3 to illustrate the differences in fold-change species expression (X-axis) versus significance for an individual species (Y-axis) (FIG. 1). Expression patterns of lncRNAs (FIG. 3; top two panels) and mRNAs (FIG. 3; bottom two panels) were compared in (1) healthy control subjects versus the MS-established cohort and (2) MS-naïve versus the CIS→MS cohort. Y-axes are log 10 p-values and x-axes are expression ratios, log 2. Comparison of the log 2 fold-change differences in healthy control versus MS-established found 1,859 differentially expressed mRNAs and 752 annotated lncRNAs. In the MS-naïve versus the CIS→MS cohort, 818 mRNAs and 149 annotated lncRNAs were differentially expressed. Differences in expression of lncRNAs were found that ranged in magnitude from $2^2$ to $2^5$ or 4-fold to 32-fold in the different cohorts while differences in expression of mRNAs were typically <$2^2$ or <4-fold. Additional analysis of the differentially expressed lncRNAs and mRNAs assessed using DESeq2 found that 49% and 61% of the lncRNAs in the MS-Naïve versus MS→CIS and MSestablished versus CTRL cohorts, respectively, had greater than a 2-fold change in species expression (FIG. 4). In contrast, only ~1% and 2% of the mRNAs in the same cohorts exhibited a 2-fold change or greater in mRNA expression levels. Plots in FIG. 4 show the percentage of differentially expressed (DE) species as a function of >1 or <1 fold change expression ratios, log 2, across annotated lncRNAs (left) and mRNAs (right). Differentially expressed species all have an adjusted p value<0.05 for across two experimental comparisons: (1) MSNaïve versus CIS→MS and (2) MS-established versus healthy control (CTRL) subjects. Accordingly, the lncRNA expression profile was determined to be more dynamic than the mRNA expression profile across the subjects examined using whole genome RNA sequencing. Therefore, lncRNA levels have greater ability to discriminate between case and control cohorts as well as case and disease control cohorts and can produce tests with improved capacity to classify disease and control groups.

Example 2

Figure 5:
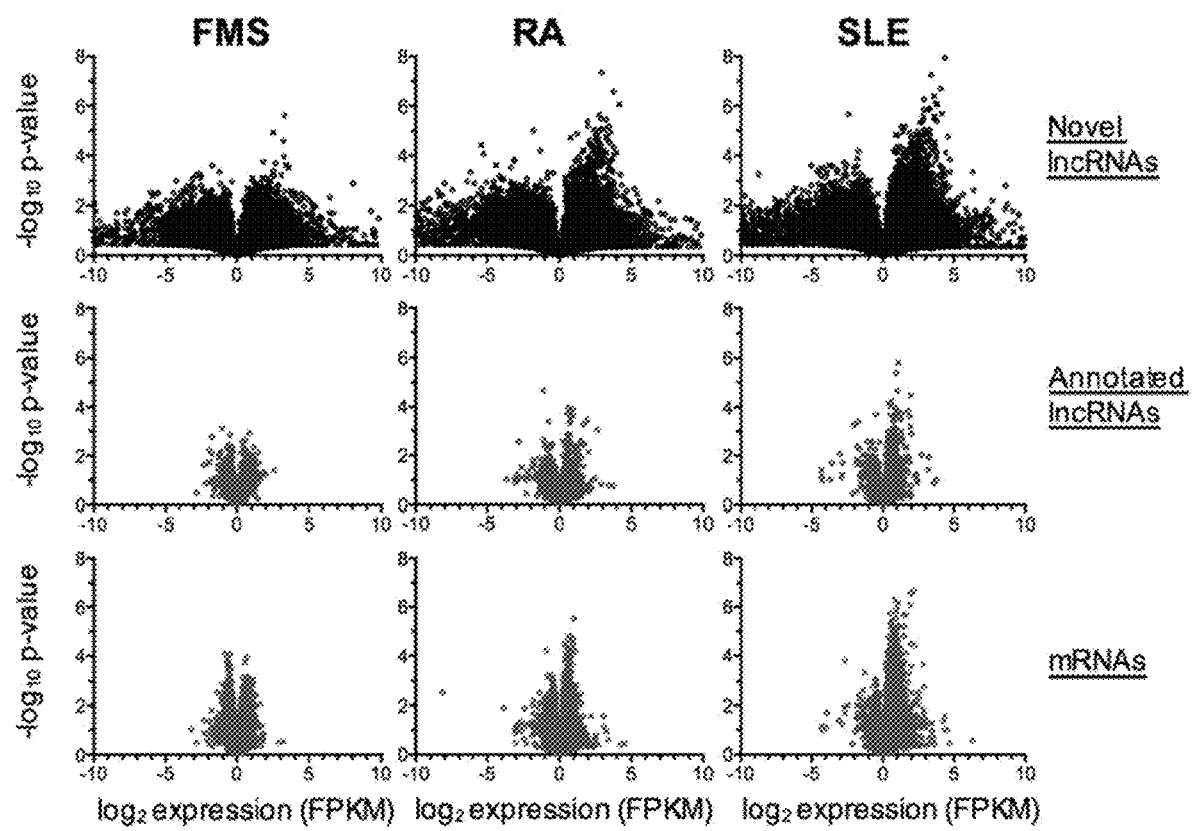
FIG. 5 shows Differential expression of novel lncRNAs, annotated lncRNAs, and mRNAs in FMS, RA, and SLE.

Peripheral whole blood was collected into PAXgene tubes from healthy control subjects (N=8), and subjects diagnosed with FMS (n=6), RA (n=6), or SLE (n=6). Subjects included in these cohorts had bloods sample obtained at the time of diagnosis. Subjects were subsequently tracked using electronic medical records for a period of 3 years and the diagnoses did not change. Total RNA from PAXgene tubes was used to prepare sequencing libraries using the Illumina Tru-Seq RNA kit with oligo-dT as the primer. 100 bp paired-end reads were generated with an Illumina Hi-Seq 2500. A quality control step was initially performed using tools such as Fastx Toolkit and FastQC. The RNA data were aligned with TopHat2 and species expression levels were quantified using Cufflinks and are reported as FPKM (fragments per kilobase per million reads). Differentially expressed species were determined using DESeq2. False discovery rate (FDR<0.05) was used for multiple test correction. GTF files for mRNAs and annotated lncRNAs were obtained from GENCODE (release 19; GRCh37.p13). Novel lncRNAs were identified using established methodologies (36). A 0.5 FPKM cutoff was used for lncRNAs and mRNAs across these sequencing data. Volcano plots were used to illustrate differences in fold-change species expression (X-axis) versus significance for an individual species (Y-axis) (FIG. 5). Expression patterns of novel lncRNAs (FIG. 5; top two plots), annotated lncRNAs (FIG. 5; middle two plots), and mRNAs (FIG. 5; bottom two plots) were compared in (1) healthy control subjects versus the FMS cohort, (2) healthy controls versus RA, (3) healthy controls versus SLE, (4) FMS versus RA, (5) FMS versus SLE, and (6) RA versus SLE (4-6 not shown). Composites of differentially expressed novel lncRNAs, annotated lncRNAs, and mRNAs across these comparisons is shown in FIG. 5. Plots shown in FIG. 5 are the percentage of differentially expressed (DE) species as a function of >2 or <2 fold change (FC) expression ratios, log 2, mRNAs (left), annotated lncRNAs (middle) and novel lncRNAs (right). Differentially expressed species all have an adjusted p value<0.05 across six experimental comparisons. *=p<0.05 comparing lncRNAs>2 log 2 FC to mRNAs>2 log 2 FC.

Figure 6:
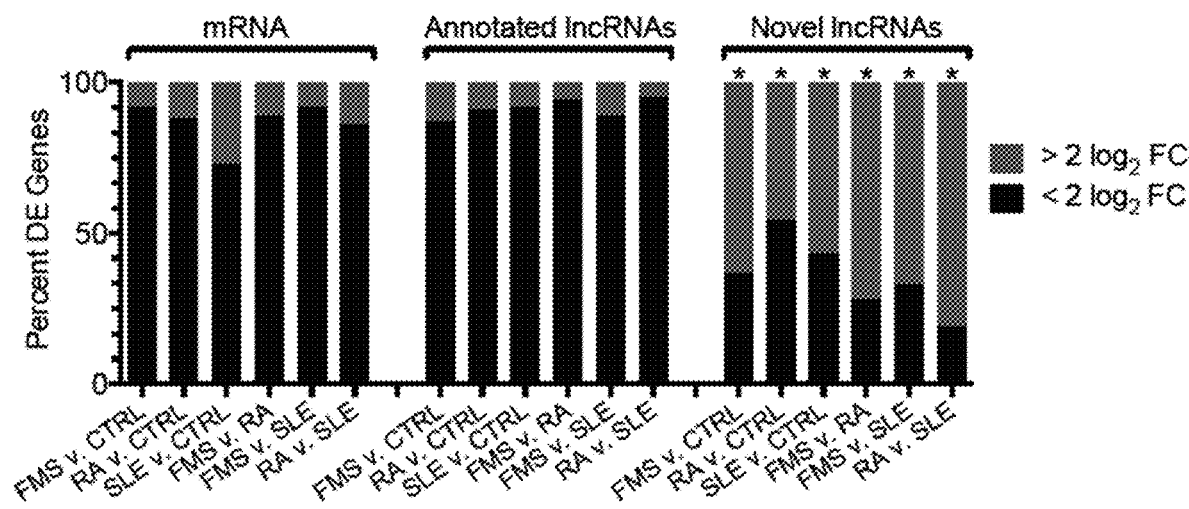
FIG. 6 shows magnitude of fold-change differences across mRNA and lncRNA species in FMS, RA, and SLE.

Comparison of the log 2 fold-change differences across these cohorts resulted in identification of 389 mRNAs and 3,317 lncRNAs (FMS vs. CTRL); 1,015 mRNAs and 1,538 lncRNAs (RA vs. CTRL); 2,003 mRNAs and 1,394 lncRNAs (SLE vs. CTRL); 542 mRNAs and 2,193 lncRNAs (FMS vs. RA); 467 mRNAs and 2,203 lncRNAs (FMS vs. SLE); and 632 mRNAs and 3,107 lncRNAs (RA vs. SLE). Differences in expression of lncRNAs ranged in magnitude from $2^2$ to $2^{10}$ or 4-fold to 1000-fold in the different cohorts while differences in expression of mRNAs were typically <$2^2$ or <4-fold. Additional analysis of the differentially expressed lncRNAs and mRNAs assessed using DESeq2 found that 63%, 46%, 57%, 72%, 67%, and 81% of the lncRNAs in the FMS vs. CTRL, RA vs. CTRL, SLE vs. CTRL, FMS vs. RA, FMS vs. SLE, and RA vs. SLE comparisons, respectively, had greater than a 4-fold difference in species expression (FIG. 6). In contrast, only 8%, 12%, 27%, 11%, 8%, and 14% of the mRNAs in the same cohorts exhibited a 4-fold difference or greater in mRNA levels. Thus, lncRNA expression profiles were more dynamic than mRNA expression profiles across the subjects examined using whole genome RNA sequencing. Therefore, lncRNA levels have greater ability to discriminate between case and control cohorts as well as case and disease control cohorts and we will be able to produce tests with improved capacity to classify disease and control groups.

Example 3

From RNA-seq analysis of the expression results obtained in Example 1, about 190 candidate lncRNAs differentially expressed between one, two or three MS cohorts and CTRL were identified. Primer pairs were designed for each lncRNA. Those candidate lncRNAs were then evaluated using RT-PCR. The following selection criteria was used:

(1) average cycle threshold, Ct, <32 after RNA isolation from a cell sample, cDNA synthesis and PCR amplification, (2) amplicon was a single band detected on agarose gels of the correct size, (3) coefficient of variance<2.0 among multiple replicates (standard deviation/mean) and (4) amplicon sequence verification. Reproducibility of replicates has been found to suffer in mRNA differential expression analysis if the Ct>32. Coefficient of variance (C.V.) is another indicator of this but it is also an indicator of primer efficiency. From the above analyses, 46 lncRNAs were identified for which the differential expression was measured among MS cohorts and CTRL (Table 4).

The ENSEMBL species identifier number is shown in the left column and Average expression (29) of each lncRNA in a cell line (Jurkat) is shown in the next column followed by the coefficient of variance (C.V.). All amplicon sequences were successfully verified.

Ratios are CASE/CTRL means, log 2: number of subject samples; CTRL, N=80; MS-C, N=40; MS-N, N=40; MS-E, N=100. Q-values were determined and bold numbers designate values that were found to be statistically significant after correction for false discovery rates using Benjamini-Hochberg correction methods.

All samples were treated as follows: 1) after obtaining informed consent, blood was collected from subjects into PAXgene tubes (PAXgene tubes were stored according to manufacturer's guidelines), 2) total RNA was purified using PAXgene RNA isolation kits, 3) RNA amounts were measured using a Nanodrop spectrophotometer, 4) cDNA synthesis was performed using oligo-dT primers and Superscript 3 (Invitrogen), 5) PCR reactions were performed in 384-well plates in 10 microliter volumes containing 1 ng/µl cDNA, Taqman master mix and SYBR green.

Expression levels of these lncRNAs were compared in the different RRMS cohorts, MS-C, MS-N, and MSE to CTRL using GAPDH expression for normalization using the formula, 2(GAPDH Ct-test Ct). Results were expressed as the ratio between the disease cohorts and CTRL cohorts, log 2. In general, most lncRNAs were under-expressed rather than over-expressed in the MS cohorts compared to CTRL cohorts. Some lncRNAs were under-expressed by over 16-fold in at least one MS cohort compared to the control cohort. Differential expression of many of the lncRNAs was similar in the different MS cohorts compared to the CTRL cohort. However, some lncRNAs were differentially expressed in only one or two MS cohorts compared to the CTRL cohort. This is consistent with MS disease progression in which inflammatory processes are most pronounced early in the disease and may indicate a role for certain lncRNAs in the inflammatory processes.

Example 4

Figure 7:
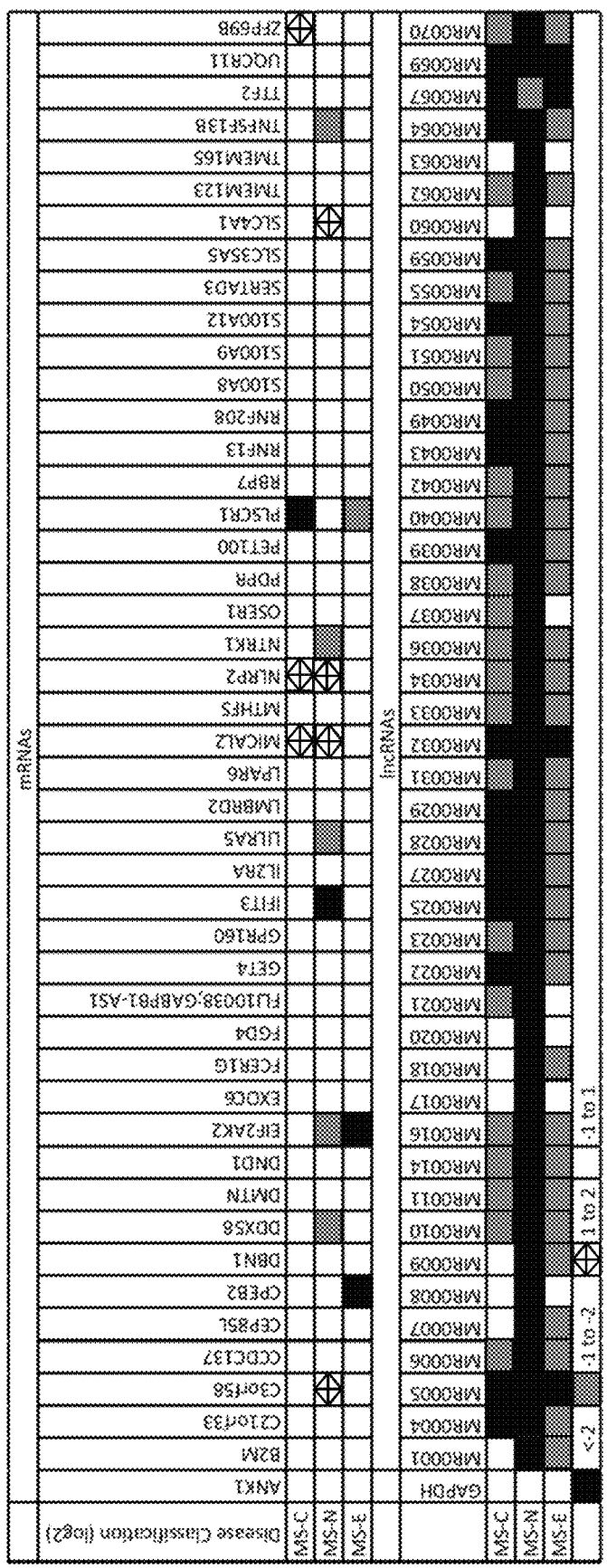
FIG. 7 shows levels of differential expression of select mRNAs and lncRNAs between indicated MS cohorts and CTRL cohorts.

To confirm that lncRNAs display greater differential expression between CASE/CTRL cohorts than mRNAs, whole genome RNA-seq was performed to identify differentially expressed mRNAs in blood in cohorts of CTRL (N=8), MS-C(N=6), MS-N(N=6), MS-E (N=8). 46 target mRNAs were picked and GAPDH was included as a housekeeping gene. TLDA plates cards were designed and expression of the target mRNAs was analyzed in a larger cohort of about 1200 subjects including healthy controls, disease controls and subjects with MS. Testing machine learning algorithms were developed from this dataset. From the RNA-seq analysis, candidate lncRNAs were identified as described above. Levels of differential expression of the mRNAs were compared to lncRNAs selected from the RNA-seq experiment in larger cohorts to. To do so, the heatmap shown in FIG. 7 illustrates the level of differential expression of the selected mRNAs and lncRNAs in each MS cohort compared to the CTRL cohort. Results are expressed as case/control ratios, log 2 and represented as shown in the legend of FIG. 7 (<−2, −1 to −2, 1 to 2, or −1 to 1). LncRNA expression data were as shown in Table 7. The results demonstrate that levels of differential expression of the selected lncRNAs was much greater than the levels of differential expression of the selected mRNAs in these same MS samples.

Example 5

Figure 10B:
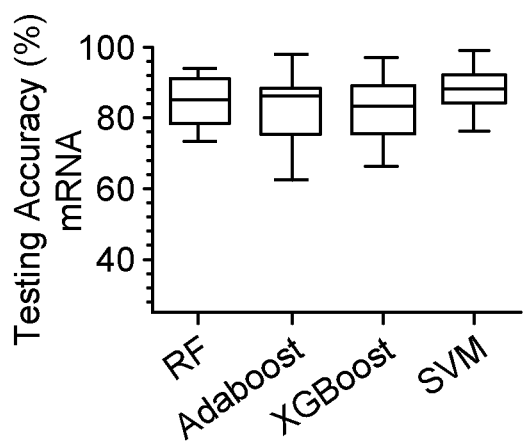
FIG. 10B depicts the testing accuracy of the machine learning methods for mRNA.
Figure 10C:
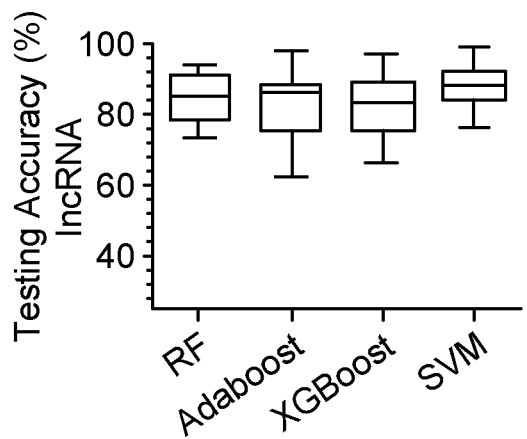
FIG. 10C depicts the testing accuracy of the machine learning methods for lncRNA.
Figure 10D:
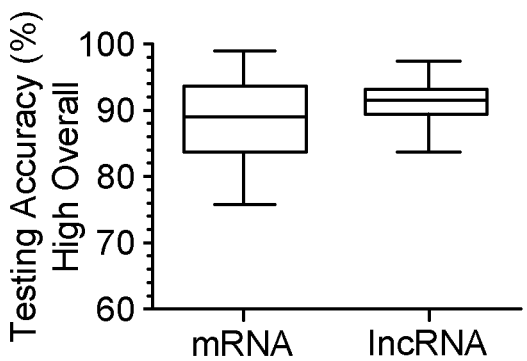
FIG. 10D depicts the highest overall testing accuracies.
Figure 10E:
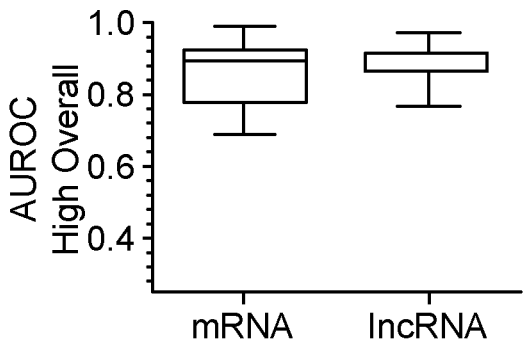
FIG. 10E depicts the AUROC of the application overall for both mRNA and lncRNA.

Peripheral whole blood samples were obtained for a population of 1,009 cases comprising CTRL, healthy subjects with no family history of autoimmune disease; CTRL-UFM, unaffected family members of subjects with MS; CISMS, subjects with a clinically isolated syndrome (CIS) who received a formal diagnosis of MS at a later date; MS-NAIVE, patients with a diagnosis of MS prior to the initiation of therapies; MS-EST, subjects with established MS on medicines; OND, other neurologic disease, inflammatory (I) or non-inflammatory (NI). Whole genome RNA sequencing and data analysis was applied using methods described above to identify both differentially expressed lncRNAs and mRNAs. A ratioscore algorithm (as described above) was applied to pairs of differentially expressed lncRNAs and pairs of differentially expressed mRNAs to generate input data for machine learning systems. 21 binary comparisons were performed separately using mRNA and lncRNA expression as shown in FIG. 10A using 75% of the dataset for training and 25% for validation testing. Random Forests, AdaBoost, XGBoost, and SVM were each trained as binary classifiers and evaluated on the validation data. FIG. 10A shows the number of ratios and accuracies for each binary comparison using the ratioscore algorithm and the highest overall accuracies obtained from one of four machine learning classifiers: random forest (RF), AdaBoost, XGBoost, or support vector machine (SVM) with the validation testing set using mRNA (left column) or lncRNA (right column) data. The area under receiver operator characteristic (ROC) curves were also determined for the machine learning methods that produced the best overall accuracy according to each case/control comparison. FIG. 10B and FIG. 10C are box and whisker plots showing validation testing accuracies for each binary comparison using four machine learning classifiers with mRNA data (FIG. 11B) or lncRNA data (FIG. 11C). FIG. 10D and FIG. 10E are box and whisker plots depicting highest overall testing accuracies (FIG. 11D) and area under the ROC curves (FIG. 11E) using the validation testing set.

Example 6

Binary classification inputs derived from CTRL, CTRL-UFM (unaffected family members of subjects with MS), MS (subjects with a clinically isolated syndrome (CIS) who received a formal diagnosis of MS at a later date), OND-I (other inflammatory neurological conditions), or OND-NI (other non-inflammatory neurological conditions) subjects were used as inputs to train and test different combinations of machine learning methods capable of multi-class discrimination (e.g., hybrid classifiers as described above). FIG. 11A, FIG. 11B, FIG. 11C, and FIG. 11D show results of the application of the trained hybrid classifier to a test data set for used for validation. FIG. 11A and FIG. 11B show ROC curves and calculated area under the ROC curve values for optimal multi-category classifier combinations capable of discriminating MS vs. CTRL or OND using mRNA (FIG. 11A) or lncRNA (FIG. 11B) datasets. FIG. 11C is a diagram illustrating trends in confidence of MS machine learning predictions using lncRNA and mRNA species expression datasets. FIG. 11D summarizing accuracy, sensitivity, and specificity of MS, OND-I, or OND-NI multi-category classifiers using the validation testing set.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

TABLE 1

Primers targeting lncRNAs in PMS

| Target lncRNA species (IQuity ID) | Forward Primer | Reverse Primer |
|---|---|---|
| RH002 | SEQ ID NO 1: AAGGCACAGAGCCAAGAAGT | SEQ ID NO 2: CAGTGCCCAGAGCTATGCTT |
| RH003 | SEQ ID NO 3: TGGTTGTCAGGGGATAGGAG | SEQ ID NO 4: CTGTCACCACCATTGAGCAC |
| RH004 | SEQ ID NO 5: GGGGACCAAAAACTGTCAGA | SEQ ID NO 6: GCATGATCAAATCATCCCCTA |
| RH006 | SEQ ID NO 7: CTGGCCTCTGACATGAACAA | SEQ ID NO 8: AGCTGCCCATTGCATCTATT |
| RH008 | SEQ ID NO 9: ATCCACAGGGGTCACAGC | SEQ ID NO 10: GAGGGCCAATGGGAACTT |
| RH010 | SEQ ID NO 11: GGCAGGACCACAGTGATGAT | SEQ ID NO 12: CAATTCGCCATGTCTCTCTG |
| RH011 | SEQ ID NO 13: GCATTAAGGAGCCCACAGAG | SEQ ID NO 14: ACCTGGCTCCACCTCCTACT |
| RH012 | SEQ ID NO 15: GAGGTTGGAGGATCACTTGG | SEQ ID NO 16: TCTGGGTGGGTTCATTTCTC |
| RH013 | SEQ ID NO 17: TTCTTTTCAAAGTCGTGTGGA | SEQ ID NO 18: TGGATGGAAAATTGTGAGCA |
| RH014 | SEQ ID NO 19: CGCCTCAGCCTTCTAAAGTG | SEQ ID NO 20: ACTCTCCAGAGTGGCACCAG |
| RH015 | SEQ ID NO 21: TCACGATTCAGTCGCAATTC | SEQ ID NO 22: CACAGAGCAGGGCATAATGA |
| RH017 | SEQ ID NO 23: TGCTCATGGAGCAGAATCAG | SEQ ID NO 24: TCTTCCCACCAGGAAATCAC |

TABLE 2

Primers targeting lncRNAs in RA

| Target lncRNA species (IQuity ID) | Forward Primer | Reverse Primer |
|---|---|---|
| RH018 | SEQ ID NO 25: TCACCCACTACCCTCTCCTG | SEQ ID NO 26: TGAAATGTGGCATTCCTACG |
| RH019 | SEQ ID NO 27: CATGGGGCTATTTGGAGAAA | SEQ ID NO 28: CACCACTGGTTCCTGGCTAT |
| RH020 | SEQ ID NO 29: GGGCTTGAACTTTGGTTCTG | SEQ ID NO 30: GTTGGGAGGAGCCTATGAT |
| RH022 | SEQ ID NO 31: CTGGAAAATTGAAAGAACAGACA | SEQ ID NO 32: TTCTTTTTCCTTATGCTATGTTGC |

TABLE 2-continued

Primers targeting lncRNAs in RA

| Target lncRNA species (IQuity ID) | Forward Primer | Reverse Primer |
|---|---|---|
| RH023 | SEQ ID NO 33: CCACGTGTATCAAGAGACATCA | SEQ ID NO 34: TTTGATGCCCTTATCATTCC |
| RH024 | SEQ ID NO 35: TGGATATTTGGTCTGCGTAGTG | SEQ ID NO 36: CAGGCTGGTCTCAAAGTCCT |
| RH025 | SEQ ID NO 37: GAGAATGCTCCTGCCTCATC | SEQ ID NO 38: CCAGGTGCACAAAGAAATCA |
| RH026 | SEQ ID NO 39: TGCGGCTGGAGGAGTTAATA | SEQ ID NO 40: CGCCTCTCTCTTCCTGTCTC |
| RH029 | SEQ ID NO 41: CTTCCCTCGTTTCTTTGCTG | SEQ ID NO 42: ACCTCTCCTGGCCCTATGAT |
| RH030 | SEQ ID NO 43: GAACAGGGGAAGGGAGAAAG | SEQ ID NO 44: GCCACCAAAGGCTATACCAA |
| RH031 | SEQ ID NO 45: CAGGAAGAAGTGCATGTTGG | SEQ ID NO 46: AGAGCTCTGGGAGGGACAC |
| RH032 | SEQ ID NO 47: CCCAGGGGTCTGATAATTCA | SEQ ID NO 48: ATGCATAGGGGACGAAAACA |
| RH033 | SEQ ID NO 49: CTTTGCCCCACCTTTAAACA | SEQ ID NO 50: ATAGCATGTGATGGGGCTTC |
| RH035 | SEQ ID NO 51: AAGCTATGTGAAGCATTTTGAGC | SEQ ID NO 52: CCAGCCAAGGTCTCCTCTTT |
| RH036 | SEQ ID NO 53: CCTGTAGTCCCTCCAAGCAG | SEQ ID NO 54: GCTGTGTGTTCCAGGTGAGA |
| RH038 | SEQ ID NO 55: CAATGGCTGTTTCATCCTCA | SEQ ID NO 56: CCTTACTGGGTGACAGGAAAA |

TABLE 3

Primers targeting lncRNAs in SLE

| Target lncRNA species (IQuity ID) | Forward Primer | Reverse Primer |
|---|---|---|
| RH039 | SEQ ID NO 57: TTTTGTGCTTCTCTGCCAAG | SEQ ID NO 58: TGTGTGCAAACTAAGTGCCAAT |
| RH040 | SEQ ID NO 59: TGGCTTGGAGAAAGGAGAGA | SEQ ID NO 60: GGCAAAAGGAAGTCCATTCA |
| RH041 | SEQ ID NO 61: TTTTCCCAAATCCCAATCAA | SEQ ID NO 62: ACAACCGGGGTTCTTTTACC |
| RH043 | SEQ ID NO 63: GGTGGAAACCTGACAAATGG | SEQ ID NO 64: CCAGGAAGGTCAGATTCCAA |
| RH044 | SEQ ID NO 65: GCTGGGTACGGTAAAGGACA | SEQ ID NO 66: CTGGGAAAGGAACACCTGAA |
| RH045 | SEQ ID NO 67: GGTTGAGGCCACTGCTTTAC | SEQ ID NO 68: CCCAGCTGAAGAGATTGGAA |
| RH046 | SEQ ID NO 69: TTTCCCTGTGTCTTCCATCC | SEQ ID NO 70: AAAAGCTGCAGAAGCCAGAG |
| RH047 | SEQ ID NO 71: TTTTTCTTGGATGCCTGGAC | SEQ ID NO 72: ATCTCTCCCTCCCCAAGTGT |
| RH049 | SEQ ID NO 73: TGCCCACACTGTTTATTGCT | SEQ ID NO 74: CACTTTGGGAGGAACTCGAA |

TABLE 3-continued

Primers targeting lncRNAs in SLE

| Target lncRNA species (IQuity ID) | Forward Primer | Reverse Primer |
|---|---|---|
| RH050 | SEQ ID NO 75: GTAGGGGCTGTCCGTATCAA | SEQ ID NO 76: ATTTCCCCACAGCTCTTCCT |
| RH051 | SEQ ID NO 77: ACAGATGCTGCCCTCTGTG | SEQ ID NO 78: AAGCCCAGGACTCTCCTCAT |
| RH053 | SEQ ID NO 79: AGTGAAACAGCCAGTGCAAA | SEQ ID NO 80: CTGGTTGCTCTGCTCTACCC |
| RH054 | SEQ ID NO 81: GTATGGTGCACTGGGGATTC | SEQ ID NO 82: CCCCTTCCTATGCCTCAAAG |
| RH055 | SEQ ID NO 83: TAGGTGAAAATGCCCCAAAA | SEQ ID NO 84: CATTTCGCTGAAGCTTGTGT |
| RH057 | SEQ ID NO 85: CCATGCAATGATTGTTTTGC | SEQ ID NO 86: CAAATGTGTATGTTTGTATGGTGGT |
| RH058 | SEQ ID NO 87: TCCTTTTTGTAATGGGAAGTGAA | SEQ ID NO 88: TACGTGTAGCCCCACCTAAG |
| RH059 | SEQ ID NO 89: TGTCCTCAAAACCCACACAA | SEQ ID NO 90: AGAGCGCGTGTGAGACTGTA |
| RH061 | SEQ ID NO 91: AGAATTTGCTGCCTGCTTGT | SEQ ID NO 92: GCTGGGGAGGTAAAGTGAAA |

TABLE 4

Differentially Expressed lncRNA species in MS

| LncRNA species ensembl identifier | avg. Ct | C.V. | MS-C/CTRL (log$_2$ ratio) | MS-N/CTRL (log$_2$ ratio) | MS-E/CTRL (log$_2$ ratio) |
|---|---|---|---|---|---|
| ENSG00000111640 (GAPDH) | 15.57 | 0.30 | 0.02 | 0.02 | 0.00 |
| ENSG00000272288 | 21.80 | 0.32 | −0.74 | −3.82 | −1.24 |
| ENSG00000237017 | 26.25 | 0.40 | −3.27 | −4.03 | −1.93 |
| ENSG00000237017 | 31.37 | 1.20 | −4.23 | −4.12 | −2.23 |
| ENSG00000249096 | 25.81 | 0.42 | −1.61 | −3.61 | −1.39 |
| ENSG00000271870 | 22.30 | 0.62 | 0.17 | −3.53 | −1.33 |
| ENSG00000272579 | 20.18 | 0.11 | 0.90 | −2.88 | −0.87 |
| ENSG00000233223 | 23.73 | 0.26 | −0.90 | −3.62 | −1.35 |
| ENSG00000267321 | 22.84 | 0.22 | −1.06 | −3.85 | −1.35 |
| ENSG00000267321 | 25.54 | 0.41 | −1.70 | −4.00 | −1.74 |
| ENSG00000263065 | 27.73 | 0.85 | −1.45 | −4.10 | −1.68 |
| ENSG00000228395 | 24.72 | 0.52 | −1.78 | −3.96 | −1.76 |
| ENSG00000264304 | 24.96 | 0.59 | 0.68 | −2.96 | −0.01 |
| ENSG00000261207 | 25.31 | 0.50 | −0.71 | −3.82 | −1.46 |
| ENSG00000245060 | 26.59 | 0.37 | 0.83 | −2.69 | −0.36 |
| ENSG00000228140 | 28.30 | 0.57 | −1.59 | −2.01 | 0.11 |
| ENSG00000228140 | 27.11 | 0.33 | −2.78 | −3.44 | −1.27 |
| ENSG00000261346 | 27.34 | 0.73 | −1.43 | −3.74 | −1.63 |
| ENSG00000242258 | 26.62 | 0.69 | −2.79 | −3.95 | −1.74 |
| ENSG00000272462 | 24.83 | 0.45 | −1.97 | −3.29 | −1.07 |
| ENSG00000272462 | 24.31 | 0.54 | −2.59 | −3.96 | −1.81 |
| ENSG00000225963 | 24.75 | 0.37 | −3.33 | −4.40 | −1.87 |
| ENSG00000267194 | 23.75 | 0.63 | −1.41 | −3.35 | −1.54 |
| ENSG00000260219 | 25.00 | 0.55 | −2.63 | −4.19 | −1.99 |
| ENSG00000260219 | 24.96 | 0.50 | −1.59 | −3.87 | −1.50 |
| ENSG00000237424 | 21.30 | 0.39 | −1.09 | −3.65 | −1.23 |
| ENSG00000249684 | 29.28 | 0.45 | −1.43 | −3.62 | −1.56 |
| ENSG00000273265 | 26.19 | 0.88 | −1.15 | −3.42 | −0.84 |
| ENSG00000273265 | 24.91 | 0.85 | −1.38 | −3.64 | −1.26 |
| ENSG00000256072 | 25.37 | 0.21 | −3.85 | −4.16 | −1.77 |
| ENSG00000272955 | 27.12 | 0.77 | −1.11 | −3.07 | −1.73 |
| ENSG00000251580 | 23.95 | 0.38 | −1.31 | −3.44 | −1.17 |
| ENSG00000272782 | 26.61 | 0.48 | −2.07 | −3.89 | −1.62 |
| ENSG00000260496 | 29.31 | 0.62 | −4.19 | −4.12 | −1.69 |
| ENSG00000260496 | 29.01 | 1.67 | −1.23 | −3.86 | −1.35 |

TABLE 4-continued

Differentially Expressed lncRNA species in MS

| LncRNA species ensembl identifier | avg. Ct | C.V. | MS-C/CTRL (log$_2$ ratio) | MS-N/CTRL (log$_2$ ratio) | MS-E/CTRL (log$_2$ ratio) |
|---|---|---|---|---|---|
| ENSG00000271122 | 22.90 | 0.57 | −1.65 | −4.23 | −1.56 |
| ENSG00000223768 | 21.54 | 0.14 | −2.40 | −4.09 | −1.80 |
| ENSG00000223768 | 22.55 | 0.97 | −1.50 | −4.10 | −1.81 |
| ENSG00000262312 | 27.07 | 0.55 | −2.00 | −4.05 | −1.76 |
| ENSG00000244879 | 22.74 | 0.63 | 0.67 | −3.16 | −0.67 |
| ENSG00000223396 | 22.06 | 0.27 | −1.68 | −3.76 | −1.37 |
| ENSG00000257270 | 21.65 | 0.53 | −0.13 | −2.96 | −0.82 |
| ENSG00000258768 | 24.67 | 0.39 | −3.16 | −4.14 | −1.70 |
| ENSG00000243368 | 26.50 | 1.53 | −3.06 | −1.61 | −2.15 |
| ENSG00000224888 | 27.88 | 0.59 | −2.91 | −3.96 | −2.07 |
| ENSG00000258302 | 23.68 | 0.47 | −1.39 | −3.95 | −1.55 |

---

What is claimed is:

1. A method of identifying presence or absence of a disease, the method comprising:

conducting an assay on RNA obtained from a patient sample to measure expression levels in the sample of one or more long non-coding RNA (lncRNA) species selected from the group consisting of ENSG00000272288, ENSG00000237017, ENSG00000249096, ENSG00000271870, ENSG00000272579, ENSG00000233223, ENSG00000267321, ENSG00000263065, ENSG00000228395, ENSG00000264304, ENSG00000261207, ENSG00000245060, ENSG00000228140, ENSG00000261346, ENSG00000242258, ENSG00000272462, ENSG00000225963, ENSG00000267194, ENSG00000260219, ENSG00000237424, ENSG00000249684, ENSG00000273265, ENSG00000256072, ENSG00000272955, ENSG00000251580, ENSG00000272782, ENSG00000260496, ENSG00000271122, ENSG00000223768, ENSG00000262312, ENSG00000244879, ENSG00000223396, ENSG00000257270, ENSG00000258768, ENSG00000243368, ENSG00000224888, and ENSG00000258302;

diagnosing the patient with multiple sclerosis where the expression levels of the one or more lncRNA differs by a statistically-significant amount from a reference expression level of said lncRNA; and treating the patient with a therapy selected from the group consisting of ocrelizumab, beta interferons, glatiramer acetate, dimethyl fumarate, fingolimod, teriflunomide, natalizumab, alemtuzumab, and mitoxantrone after diagnosing the patient with multiple sclerosis.

2. The method of claim 1, comprising measuring expression levels of a plurality of lncRNA species.

3. The method of claim 1, wherein the patient sample is selected from the group consisting of blood, serum, saliva, sputum, urine, semen, transvaginal fluid, cerebrospinal fluid, sweat, stool, a cell or a tissue biopsy.

4. The method of claim 1, further comprising conducting an assay to measure an expression level of a housekeeping gene and normalizing the expression level of the lncRNA to the expression level of the housekeeping gene.

5. The method of claim 4, wherein the housekeeping gene is selected from the group consisting of GAPDH, ACTB, B2M, 18S, and 28S.

6. The method of claim 1, wherein the assay comprises a reverse transcription polymerase chain reaction (RT-PCR).

* * * * *

SEQUENCE LISTING

<160> NUMBER OF SEQ ID NOS: 92

<210> SEQ ID NO 1
<211> LENGTH: 20
<212> TYPE: DNA
<213> ORGANISM: Homo sapiens

<400> SEQUENCE: 1
aaggcacaga gccaagaagt        20

<210> SEQ ID NO 2
<211> LENGTH: 20
<212> TYPE: DNA
<213> ORGANISM: Homo sapiens

<400> SEQUENCE: 2
cagtgcccag agctatgctt        20

<210> SEQ ID NO 3
<211> LENGTH: 19
<212> TYPE: DNA
<213> ORGANISM: Homo sapiens

<400> SEQUENCE: 3
ggttgtcagg ggataggag        19

<210> SEQ ID NO 4
<211> LENGTH: 20
<212> TYPE: DNA
<213> ORGANISM: Homo sapiens

<400> SEQUENCE: 4
ctgtcaccac cattgagcac        20

<210> SEQ ID NO 5
<211> LENGTH: 20
<212> TYPE: DNA
<213> ORGANISM: Homo sapiens

<400> SEQUENCE: 5
ggggaccaaa aactgtcaga        20

<210> SEQ ID NO 6
<211> LENGTH: 21
<212> TYPE: DNA
<213> ORGANISM: Homo sapiens

```
<400> SEQUENCE: 6
gcatgatcaa atcatcccct a                                              21

<210> SEQ ID NO 7
<211> LENGTH: 20
<212> TYPE: DNA
<213> ORGANISM: Homo sapiens

<400> SEQUENCE: 7
ctggcctctg acatgaacaa                                                20

<210> SEQ ID NO 8
<211> LENGTH: 20
<212> TYPE: DNA
<213> ORGANISM: Homo sapiens

<400> SEQUENCE: 8
agctgcccat tgcatctatt                                                20

<210> SEQ ID NO 9
<211> LENGTH: 18
<212> TYPE: DNA
<213> ORGANISM: Homo sapiens

<400> SEQUENCE: 9
atccacaggg gtcacagc                                                  18

<210> SEQ ID NO 10
<211> LENGTH: 18
<212> TYPE: DNA
<213> ORGANISM: Homo sapiens

<400> SEQUENCE: 10
gagggccaat gggaactt                                                  18

<210> SEQ ID NO 11
<211> LENGTH: 20
<212> TYPE: DNA
<213> ORGANISM: Homo sapiens

<400> SEQUENCE: 11
ggcaggacca cagtgatgat                                                20

<210> SEQ ID NO 12
<211> LENGTH: 20
<212> TYPE: DNA
<213> ORGANISM: Homo sapiens

<400> SEQUENCE: 12
caattcgcca tgtctctctg                                                20

<210> SEQ ID NO 13
<211> LENGTH: 20
<212> TYPE: DNA
<213> ORGANISM: Homo sapiens

<400> SEQUENCE: 13
gcattaagga gcccacagag                                                20

<210> SEQ ID NO 14
<211> LENGTH: 20
<212> TYPE: DNA
```

<213> ORGANISM: Homo sapiens

<400> SEQUENCE: 14
acctggctcc acctcctact                                          20

<210> SEQ ID NO 15
<211> LENGTH: 20
<212> TYPE: DNA
<213> ORGANISM: Homo sapiens

<400> SEQUENCE: 15
gaggttggag gatcacttgg                                          20

<210> SEQ ID NO 16
<211> LENGTH: 20
<212> TYPE: DNA
<213> ORGANISM: Homo sapiens

<400> SEQUENCE: 16
tctgggtggg ttcatttctc                                          20

<210> SEQ ID NO 17
<211> LENGTH: 21
<212> TYPE: DNA
<213> ORGANISM: Homo sapiens

<400> SEQUENCE: 17
ttcttttcaa agtcgtgtgg a                                        21

<210> SEQ ID NO 18
<211> LENGTH: 20
<212> TYPE: DNA
<213> ORGANISM: Homo sapiens

<400> SEQUENCE: 18
tggatggaaa attgtgagca                                          20

<210> SEQ ID NO 19
<211> LENGTH: 20
<212> TYPE: DNA
<213> ORGANISM: Homo sapiens

<400> SEQUENCE: 19
cgcctcagcc ttctaaagtg                                          20

<210> SEQ ID NO 20
<211> LENGTH: 20
<212> TYPE: DNA
<213> ORGANISM: Homo sapiens

<400> SEQUENCE: 20
actctccaga gtggcaccag                                          20

<210> SEQ ID NO 21
<211> LENGTH: 20
<212> TYPE: DNA
<213> ORGANISM: Homo sapiens

<400> SEQUENCE: 21
tcacgattca gtcgcaattc                                          20

<210> SEQ ID NO 22
<211> LENGTH: 20

```
<212> TYPE: DNA
<213> ORGANISM: Homo sapiens

<400> SEQUENCE: 22
cacagagcag ggcataatga                                               20

<210> SEQ ID NO 23
<211> LENGTH: 20
<212> TYPE: DNA
<213> ORGANISM: Homo sapiens

<400> SEQUENCE: 23
tgctcatgga gcagaatcag                                               20

<210> SEQ ID NO 24
<211> LENGTH: 20
<212> TYPE: DNA
<213> ORGANISM: Homo sapiens

<400> SEQUENCE: 24
tcttcccacc aggaaatcac                                               20

<210> SEQ ID NO 25
<211> LENGTH: 20
<212> TYPE: DNA
<213> ORGANISM: Homo sapiens

<400> SEQUENCE: 25
tcacccacta ccctctcctg                                               20

<210> SEQ ID NO 26
<211> LENGTH: 20
<212> TYPE: DNA
<213> ORGANISM: Homo sapiens

<400> SEQUENCE: 26
tgaaatgtgg cattcctacg                                               20

<210> SEQ ID NO 27
<211> LENGTH: 20
<212> TYPE: DNA
<213> ORGANISM: Homo sapiens

<400> SEQUENCE: 27
catggggcta tttggagaaa                                               20

<210> SEQ ID NO 28
<211> LENGTH: 20
<212> TYPE: DNA
<213> ORGANISM: Homo sapiens

<400> SEQUENCE: 28
caccactggt tcctggctat                                               20

<210> SEQ ID NO 29
<211> LENGTH: 20
<212> TYPE: DNA
<213> ORGANISM: Homo sapiens

<400> SEQUENCE: 29
gggcttgaac tttggttctg                                               20

<210> SEQ ID NO 30
```

```
<211> LENGTH: 20
<212> TYPE: DNA
<213> ORGANISM: Homo sapiens

<400> SEQUENCE: 30
gttggggagg agcctatgat                                               20

<210> SEQ ID NO 31
<211> LENGTH: 23
<212> TYPE: DNA
<213> ORGANISM: Homo sapiens

<400> SEQUENCE: 31
ctggaaaatt gaaagaacag aca                                           23

<210> SEQ ID NO 32
<211> LENGTH: 24
<212> TYPE: DNA
<213> ORGANISM: Homo sapiens

<400> SEQUENCE: 32 ttcttttcc ttatgctatg ttgc                                           24

<210> SEQ ID NO 33
<211> LENGTH: 22
<212> TYPE: DNA
<213> ORGANISM: Homo sapiens

<400> SEQUENCE: 33
ccacgtgtat caagagacat ca                                            22

<210> SEQ ID NO 34
<211> LENGTH: 20
<212> TYPE: DNA
<213> ORGANISM: Homo sapiens

<400> SEQUENCE: 34
tttgatgccc ttatcattcc                                               20

<210> SEQ ID NO 35
<211> LENGTH: 22
<212> TYPE: DNA
<213> ORGANISM: Homo sapiens

<400> SEQUENCE: 35
tggatatttg gtctgcgtag tg                                            22

<210> SEQ ID NO 36
<211> LENGTH: 20
<212> TYPE: DNA
<213> ORGANISM: Homo sapiens

<400> SEQUENCE: 36
caggctggtc tcaaagtcct                                               20

<210> SEQ ID NO 37
<211> LENGTH: 20
<212> TYPE: DNA
<213> ORGANISM: Homo sapiens

<400> SEQUENCE: 37
gagaatgctc ctgcctcatc                                               20
```

```
<210> SEQ ID NO 38
<211> LENGTH: 20
<212> TYPE: DNA
<213> ORGANISM: Homo sapiens

<400> SEQUENCE: 38
ccaggtgcac aaagaaatca                                               20

<210> SEQ ID NO 39
<211> LENGTH: 20
<212> TYPE: DNA
<213> ORGANISM: Homo sapiens

<400> SEQUENCE: 39
tgcggctgga ggagttaata                                               20

<210> SEQ ID NO 40
<211> LENGTH: 20
<212> TYPE: DNA
<213> ORGANISM: Homo sapiens

<400> SEQUENCE: 40
cgcctctctc ttcctgtctc                                               20

<210> SEQ ID NO 41
<211> LENGTH: 20
<212> TYPE: DNA
<213> ORGANISM: Homo sapiens

<400> SEQUENCE: 41
cttccctcgt ttctttgctg                                               20

<210> SEQ ID NO 42
<211> LENGTH: 20
<212> TYPE: DNA
<213> ORGANISM: Homo sapiens

<400> SEQUENCE: 42
acctctcctg gccctatgat                                               20

<210> SEQ ID NO 43
<211> LENGTH: 20
<212> TYPE: DNA
<213> ORGANISM: Homo sapiens

<400> SEQUENCE: 43
gaacagggga agggagaaag                                               20

<210> SEQ ID NO 44
<211> LENGTH: 20
<212> TYPE: DNA
<213> ORGANISM: Homo sapiens

<400> SEQUENCE: 44
gccaccaaag gctataccaa                                               20

<210> SEQ ID NO 45
<211> LENGTH: 20
<212> TYPE: DNA
<213> ORGANISM: Homo sapiens

<400> SEQUENCE: 45
caggaagaag tgcatgttgg                                               20
```

```
<210> SEQ ID NO 46
<211> LENGTH: 19
<212> TYPE: DNA
<213> ORGANISM: Homo sapiens

<400> SEQUENCE: 46
agagctctgg gagggacac                                                    19

<210> SEQ ID NO 47
<211> LENGTH: 20
<212> TYPE: DNA
<213> ORGANISM: Homo sapiens

<400> SEQUENCE: 47
cccaggggtc tgataattca                                                   20

<210> SEQ ID NO 48
<211> LENGTH: 20
<212> TYPE: DNA
<213> ORGANISM: Homo sapiens

<400> SEQUENCE: 48
atgcataggg gacgaaaaca                                                   20

<210> SEQ ID NO 49
<211> LENGTH: 20
<212> TYPE: DNA
<213> ORGANISM: Homo sapiens

<400> SEQUENCE: 49
ctttgcccca cctttaaaca                                                   20

<210> SEQ ID NO 50
<211> LENGTH: 20
<212> TYPE: DNA
<213> ORGANISM: Homo sapiens

<400> SEQUENCE: 50
atagcatgtg atggggcttc                                                   20

<210> SEQ ID NO 51
<211> LENGTH: 23
<212> TYPE: DNA
<213> ORGANISM: Homo sapiens

<400> SEQUENCE: 51
aagctatgtg aagcattttg agc                                               23

<210> SEQ ID NO 52
<211> LENGTH: 20
<212> TYPE: DNA
<213> ORGANISM: Homo sapiens

<400> SEQUENCE: 52
ccagccaagg tctcctcttt                                                   20

<210> SEQ ID NO 53
<211> LENGTH: 20
<212> TYPE: DNA
<213> ORGANISM: Homo sapiens

<400> SEQUENCE: 53
cctgtagtcc ctccaagcag                                                   20
```

<210> SEQ ID NO 54
<211> LENGTH: 20
<212> TYPE: DNA
<213> ORGANISM: Homo sapiens

<400> SEQUENCE: 54
gctgtgtgtt ccaggtgaga					20

<210> SEQ ID NO 55
<211> LENGTH: 20
<212> TYPE: DNA
<213> ORGANISM: Homo sapiens

<400> SEQUENCE: 55
caatggctgt ttcatcctca					20

<210> SEQ ID NO 56
<211> LENGTH: 21
<212> TYPE: DNA
<213> ORGANISM: Homo sapiens

<400> SEQUENCE: 56
ccttactggg tgacaggaaa a					21

<210> SEQ ID NO 57
<211> LENGTH: 20
<212> TYPE: DNA
<213> ORGANISM: Homo sapiens

<400> SEQUENCE: 57
ttttgtgctt ctctgccaag					20

<210> SEQ ID NO 58
<211> LENGTH: 22
<212> TYPE: DNA
<213> ORGANISM: Homo sapiens

<400> SEQUENCE: 58
tgtgtgcaaa ctaagtgcca at				22

<210> SEQ ID NO 59
<211> LENGTH: 20
<212> TYPE: DNA
<213> ORGANISM: Homo sapiens

<400> SEQUENCE: 59
tggcttggag aaaggagaga					20

<210> SEQ ID NO 60
<211> LENGTH: 20
<212> TYPE: DNA
<213> ORGANISM: Homo sapiens

<400> SEQUENCE: 60
ggcaaaagga agtccattca					20

<210> SEQ ID NO 61
<211> LENGTH: 20
<212> TYPE: DNA
<213> ORGANISM: Homo sapiens

```
<400> SEQUENCE: 61
ttttcccaaa tcccaatcaa                                               20

<210> SEQ ID NO 62
<211> LENGTH: 20
<212> TYPE: DNA
<213> ORGANISM: Homo sapiens

<400> SEQUENCE: 62
acaaccgggg ttcttttacc                                               20

<210> SEQ ID NO 63
<211> LENGTH: 20
<212> TYPE: DNA
<213> ORGANISM: Homo sapiens

<400> SEQUENCE: 63
ggtggaaacc tgacaaatgg                                               20

<210> SEQ ID NO 64
<211> LENGTH: 20
<212> TYPE: DNA
<213> ORGANISM: Homo sapiens

<400> SEQUENCE: 64
ccaggaaggt cagattccaa                                               20

<210> SEQ ID NO 65
<211> LENGTH: 20
<212> TYPE: DNA
<213> ORGANISM: Homo sapiens

<400> SEQUENCE: 65
gctgggtacg gtaaaggaca                                               20

<210> SEQ ID NO 66
<211> LENGTH: 20
<212> TYPE: DNA
<213> ORGANISM: Homo sapiens

<400> SEQUENCE: 66
ctgggaaagg aacacctgaa                                               20

<210> SEQ ID NO 67
<211> LENGTH: 20
<212> TYPE: DNA
<213> ORGANISM: Homo sapiens

<400> SEQUENCE: 67
ggttgaggcc actgctttac                                               20

<210> SEQ ID NO 68
<211> LENGTH: 20
<212> TYPE: DNA
<213> ORGANISM: Homo sapiens

<400> SEQUENCE: 68
cccagctgaa gagattggaa                                               20

<210> SEQ ID NO 69
<211> LENGTH: 20
<212> TYPE: DNA
```

<213> ORGANISM: Homo sapiens

<400> SEQUENCE: 69
tttccctgtg tcttccatcc                                          20

<210> SEQ ID NO 70
<211> LENGTH: 20
<212> TYPE: DNA
<213> ORGANISM: Homo sapiens

<400> SEQUENCE: 70
aaaagctgca gaagccagag                                          20

<210> SEQ ID NO 71
<211> LENGTH: 20
<212> TYPE: DNA
<213> ORGANISM: Homo sapiens

<400> SEQUENCE: 71
tttttcttgg atgcctggac                                          20

<210> SEQ ID NO 72
<211> LENGTH: 20
<212> TYPE: DNA
<213> ORGANISM: Homo sapiens

<400> SEQUENCE: 72
atctctccct ccccaagtgt                                          20

<210> SEQ ID NO 73
<211> LENGTH: 20
<212> TYPE: DNA
<213> ORGANISM: Homo sapiens

<400> SEQUENCE: 73
tgcccacact gtttattgct                                          20

<210> SEQ ID NO 74
<211> LENGTH: 20
<212> TYPE: DNA
<213> ORGANISM: Homo sapiens

<400> SEQUENCE: 74
cactttggga ggaactcgaa                                          20

<210> SEQ ID NO 75
<211> LENGTH: 20
<212> TYPE: DNA
<213> ORGANISM: Homo sapiens

<400> SEQUENCE: 75 gtagggctg tccgtatcaa                                           20

<210> SEQ ID NO 76
<211> LENGTH: 20
<212> TYPE: DNA
<213> ORGANISM: Homo sapiens

<400> SEQUENCE: 76
atttccccac agctcttcct                                          20

<210> SEQ ID NO 77
<211> LENGTH: 19

```
<212> TYPE: DNA
<213> ORGANISM: Homo sapiens

<400> SEQUENCE: 77
acagatgctg ccctctgtg                                               19

<210> SEQ ID NO 78
<211> LENGTH: 20
<212> TYPE: DNA
<213> ORGANISM: Homo sapiens

<400> SEQUENCE: 78
aagcccagga ctctcctcat                                              20

<210> SEQ ID NO 79
<211> LENGTH: 20
<212> TYPE: DNA
<213> ORGANISM: Homo sapiens

<400> SEQUENCE: 79
agtgaaacag ccagtgcaaa                                              20

<210> SEQ ID NO 80
<211> LENGTH: 20
<212> TYPE: DNA
<213> ORGANISM: Homo sapiens

<400> SEQUENCE: 80
ctggttgctc tgctctaccc                                              20

<210> SEQ ID NO 81
<211> LENGTH: 20
<212> TYPE: DNA
<213> ORGANISM: Homo sapiens

<400> SEQUENCE: 81
gtatggtgca ctggggattc                                              20

<210> SEQ ID NO 82
<211> LENGTH: 20
<212> TYPE: DNA
<213> ORGANISM: Homo sapiens

<400> SEQUENCE: 82
ccccttccta tgcctcaaag                                              20

<210> SEQ ID NO 83
<211> LENGTH: 20
<212> TYPE: DNA
<213> ORGANISM: Homo sapiens

<400> SEQUENCE: 83
taggtgaaaa tgccccaaaa                                              20

<210> SEQ ID NO 84
<211> LENGTH: 20
<212> TYPE: DNA
<213> ORGANISM: Homo sapiens

<400> SEQUENCE: 84
catttcgctg aagcttgtgt                                              20

<210> SEQ ID NO 85
```

```
<211> LENGTH: 20
<212> TYPE: DNA
<213> ORGANISM: Homo sapiens

<400> SEQUENCE: 85
ccatgcaatg attgttttgc                                                  20

<210> SEQ ID NO 86
<211> LENGTH: 25
<212> TYPE: DNA
<213> ORGANISM: Homo sapiens

<400> SEQUENCE: 86
caaatgtgta tgtttgtatg gtggt                                            25

<210> SEQ ID NO 87
<211> LENGTH: 23
<212> TYPE: DNA
<213> ORGANISM: Homo sapiens

<400> SEQUENCE: 87 tccttttgt aatgggaagt gaa                                               23

<210> SEQ ID NO 88
<211> LENGTH: 20
<212> TYPE: DNA
<213> ORGANISM: Homo sapiens

<400> SEQUENCE: 88
tacgtgtagc cccacctaag                                                  20

<210> SEQ ID NO 89
<211> LENGTH: 20
<212> TYPE: DNA
<213> ORGANISM: Homo sapiens

<400> SEQUENCE: 89
tgtcctcaaa acccacacaa                                                  20

<210> SEQ ID NO 90
<211> LENGTH: 20
<212> TYPE: DNA
<213> ORGANISM: Homo sapiens

<400> SEQUENCE: 90
agagcgcgtg tgagactgta                                                  20

<210> SEQ ID NO 91
<211> LENGTH: 20
<212> TYPE: DNA
<213> ORGANISM: Homo sapiens

<400> SEQUENCE: 91
agaatttgct gcctgcttgt                                                  20

<210> SEQ ID NO 92
<211> LENGTH: 20
<212> TYPE: DNA
<213> ORGANISM: Homo sapiens

<400> SEQUENCE: 92
gctggggagg taaagtgaaa                                                  20
```